US009675575B2

(12) United States Patent
Sandnes et al.

(10) Patent No.: US 9,675,575 B2
(45) Date of Patent: Jun. 13, 2017

(54) OMEGA-3 COMPOSITIONS, DOSAGE FORMS, AND METHODS OF USE

(71) Applicant: MARINE INGREDIENTS, LLC, Mount Bethel, PA (US)

(72) Inventors: Olav Sandnes, Mount Bethel, PA (US); Bruce A. Miller, Mount Bethel, PA (US); Jorn Dyerberg, Charlottenlund (DK)

(73) Assignee: Marine Ingredients, LLC, Mount Bethel, PA (US)

( * ) Notice: Subject to any disclaimer, the term of this patent is extended or adjusted under 35 U.S.C. 154(b) by 0 days.

(21) Appl. No.: 15/146,680

(22) Filed: May 4, 2016

(65) Prior Publication Data

US 2016/0243068 A1 Aug. 25, 2016

Related U.S. Application Data

(63) Continuation of application No. PCT/US2015/034372, filed on Jun. 5, 2015.

(60) Provisional application No. 62/019,289, filed on Jun. 30, 2014, provisional application No. 62/009,145, filed on Jun. 6, 2014.

(51) Int. Cl.
*A61K 31/202* (2006.01)
*A61K 35/60* (2006.01)
*A61K 35/618* (2015.01)

(52) U.S. Cl.
CPC ............ *A61K 31/202* (2013.01); *A61K 35/60* (2013.01); *A61K 35/618* (2013.01)

(58) Field of Classification Search
CPC ............................. A61K 31/202; C11C 1/005
See application file for complete search history.

(56) References Cited

U.S. PATENT DOCUMENTS

| | | | |
|---|---|---|---|
| 5,502,077 A | 3/1996 | Breivik et al. | |
| 5,656,667 A | 8/1997 | Breivik et al. | |
| 6,159,523 A * | 12/2000 | Cain | A21D 2/16 424/523 |
| 6,537,787 B1 | 3/2003 | Breton | |
| 7,652,068 B2 | 1/2010 | Feuerstein | |
| 7,824,727 B2 | 11/2010 | Hudson et al. | |
| 8,071,646 B2 | 12/2011 | Feuerstein et al. | |
| 2007/0298156 A1 | 12/2007 | Mehansho et al. | |
| 2010/0190220 A1 | 7/2010 | Furihata et al. | |
| 2010/0236137 A1 | 9/2010 | Wu et al. | |
| 2012/0252888 A1 | 10/2012 | Pantzaris et al. | |
| 2013/0137770 A1 | 5/2013 | Lewis | |
| 2013/0190521 A1 | 7/2013 | Kralovec et al. | |
| 2013/0274337 A1 | 10/2013 | Domingo Pedrol et al. | |
| 2013/0310457 A1 | 11/2013 | Ramesh | |
| 2013/0317241 A1 * | 11/2013 | Breivik | C07C 51/48 554/194 |
| 2014/0088043 A1 | 3/2014 | Hoem et al. | |
| 2014/0099345 A1 | 4/2014 | Deckelbaum et al. | |

FOREIGN PATENT DOCUMENTS

| | | |
|---|---|---|
| WO | 2007066232 A2 | 6/2007 |
| WO | 2008133573 A1 | 11/2008 |
| WO | 2010010365 A1 | 1/2010 |
| WO | 2011092299 A1 | 8/2011 |
| WO | 2013170006 A2 | 11/2013 |

OTHER PUBLICATIONS

Childs et al, Am.J.Clin.Nutr., 1990, 52:632-639.*
Woodward, et al. The association between resting heart rate, cardiovascular disease and mortality: evidence from 112,680 men and women in 12 cohorts:, European Journal of Preventive Cardiology, vol. 21(6), pp. 719-726, 2014.
World Health Organization, "Global Health Risks, Mortality and burden of disease attributable to selected major risks", WHO Library Cataloguing-in-Publication Data, 70 pages 2009.
Yang, et al. "Lipolysis of menhaden oil triacylglycerols and the corresponding fatty acid alkyl esters by pancreatic lipase in vitro: a reexamination", J. Lipid Res. 31, pp. 137-148, 1990.
Yusuf, et al. "Effect of potentially modifiable risk factos associated with myocardial infarction in 52 countries (the INTERHEART study): a case control", The Lancet, 364, pp. 937-952, 2004.
Dyerberg, et al., "Bioavailability of marine n-3 Fatty Acid formulations, Prostaglandins, Leukotrienes and Essential Fatty Acids", vol. 83, pp. 137-141, 2010.
PCT/US2015/034372, International Search Report and Written Opinion, Aug. 12, 2015.
Lerman, et al. "Correction of the Omega-3 Index in women with metabolic syndrome by adding omega-3 supplements to a Mediterranean-style diet", BMC Complementary and Alternative Medicine, 12(Suppl 1): p. 138, 2012.
Armand, "Lipases and lipolysis in the human digestive tract: where do we stand?", Current Opinion in Clinical Nutrition and Metabolic Care, 10, 2007, pp. 156-164.
Balk, et al., "Effects of Omega-3 fatty acids on serum markers of cardiovascular disease risk: A systemic review", Atherosclerosis (189), 2006, pp. 19-30.
Bang, et al., "Plasma Lipids and Lipoproteins in Greenlandic West Coast Eskimos", Acta med. scand. vol. 192, 1972, pp. 85-94.
Bang, et al., "The Composition of Food Consumed by Greenland Eskimos", Acta Med Scan, 200, 1976, pp. 69-73.
Carlier, "Digestion and absorption of polyunsaturated fatty acids", Reprod Nutr Dev 31, 1991, pp. 475-5000.
Cooney, et al., "Elevated resting heart rate is an independent risk factor for cardiovascular disease in healthy men and women", American Heart Journal, vol. 159, No. 4, 2010, pp. 612-619.e3.
Criqui, et al., "Plasma Triglyceride Level and Mortality from Coronary Heart Disease", The New England Journal of Medicine, vol. 328, No. 17, Apr. 29, 1993, pp. 1220-1225.

(Continued)

*Primary Examiner* — Sudhakar Katakam
(74) *Attorney, Agent, or Firm* — Stoel Rives LLP

(57) ABSTRACT

Omega-3 compositions, dosage forms, and methods of use are disclosed herein. The omega-3 compositions and dosage forms disclosed herein may comprise DHA and EPA at a ratio of about 5:2. The omega-3 compositions and dosage forms disclosed herein may comprise re-esterified triglycerides. Methods of treatment using the compositions and dosage forms are also disclosed.

14 Claims, 30 Drawing Sheets

(56) References Cited

OTHER PUBLICATIONS

Dangardt, et al., "Omega-3 fatty acid supplementation improves vascular function and reduces inflammation in obese adolescents", Atherosclerosis 212, 2010, pp. 580-585.
Dyerberg, et al., "Fatty acid composition of the plasma lipids in Greenland Eskimos", The American Journal of Clinical Nutrition, Sep. 28, 1975, pp. 958-966.
Dyerberg, et al., "Haemostatic Function and Platelet Polyunsaturated Fatty Acids in Eskimos", The Lancet, Sep. 1, 1979, pp. 433-435.
Gajos, et al., "Polunsaturated omega-3 fatty acids reduce lipoprotein-associated phospholipase A2 in patients with stable angina", Nutrition, Metabolism & Cardiovascular Diseases 24, 2014, pp. 434-439.
Geelen et al., "Effects of n-3 fatty acids from fish on premature vantricular complexes and heart rate in humans", Am. J. Clin. Nutr. 81, 2005, pp. 416-420.
Geleijnse, et al., "Blood pressure response to fish oil supplementation: metaregression analysis of randomized trials", Journal of Hypertension 20, 2002, pp. 1493-14999.
Harris, "Fish oils and plasma lipid and lipoprotein metabolism in humans: a critical review", Journal of Lipid Research, vol. 30, 1989, pp. 785-807.
Harris, et al., "Reduction of postprandial triglyceridemia in humans by dietary n-3 fatty acids", Journal of Lipid Research, vol. 29, 1988, pp. 1451-1460.
Harris, "The omega-3 index as a risk factor for coronary heart disease", Am. J. Clin. Nutr. 87, 2008, pp. 1997S-2002S.
Hedengran, et al., "n-3 PUFA Esterified to Glycerol or as Ethyl Esters Reduce Non-Fasting Plasma Triacylglycerol in Subjects with Hypertriglyceridemia: A Randomized Trial", AOCS, Nov. 11, 2014, 11 pages.
Jacobson, et al., "Role of n-3 fatty acids in the treatment of hypertriglyceridemia and cardiovascular disease", Am. J. Clin. Nutr. 87(suppl), 2008, pp. 1981S-1990S.
Katan, et al., "Kinetics of the incorporation of dietary fatty acids into serum cholesteryl esters, erythrocyte membrances, and adipose tissue: an 18-month controlled study", Journal of Lipid Research, vol. 38, 1997, pp. 2012-2022.
Kris-Etherton, et al., "Fish Consumption, Fish Oil, Omega-3 Fatty Acids, and Cardiovascular Disease", Circulation, AHA Scientific Statement, Nov. 19, 2002, pp. 2747-2757.
Krokan, et al., "The enteral bioavailability of eicosapentaenoic acid and docosahexaenoic acid is as good from ethyl esters as from glyceryl esters in spite of lower hydrolytic rates by pancreatic lipase in vitro", Biochimica et Biophysica Acta, 1168, 1993, pp. 59-67.
Laidlaw, et al., "A randomized clinical trial to determine the efficacy of manufacturers' recommended doses of omeda-3 fatty acids from different sources in facilitating cardiovascular disease risk reduction", Lipids in Health and Disease 13:99, 2014, 26 pages.
Lewington, et al., "Blood cholestrol and vascular mortality by age, sex, and blood pressure: a meta-analysis of individual data from 61 prospective studies with 55000 vascular deaths", The Lancet, 370, 2007, pp. 1829-1839.
Mensink, et al., "Effects of dietary fatty acids and carbohydrates on the ratio of serum total to HDL cholesterol and on serum lipids and apolipoproteins: a meta-analysis of 60 controlled trials", Am. J. Clin. Nutr. 77, 2003, pp. 1146-1155.
Metcalf, et al., "Effects of fish-oil supplementation on myocardial fatty acids in humans", Am. J. Clin. Nutr. 85, 2007, pp. 1222-1228.
Meyer, et al., "Dose-Dependent Effects of Docosahexaenoic Acid Supplementation on Blood Lipids in Statin-Treated Hyperlipidaemic Subjects", Lipids (42), 2007, pp. 109-115.
Mori, et al., "Purified eicosapentaenoic and docosahexaenoic acids have differential effects on serum lipids and lipoproteins, LDL particle size, glucose, and insulin in mildly hyperlipidemic men", Am. J. Clin. Nutr. 71, 2000, pp. 1085-1094.
Mozaffarian, et al., "Effect of Fish Oil on Heart Rate in Humans", Circulation, vol. 112, 2005, pp. 1945-1952.
National Cholesterol Education Program, "Third Report of the National Cholesterol Education Program (NCEP) Expert Panel on Detection, Evaluation, and Treatment of High Blood Cholesterol in Adults (Adult Treatment Panel III) Final Report", NIH Publication No. 02-5215, Sep. 2002, 280 pages.
Nelson, et al., "Omega-3 fatty acids and lipoprotein associated phospholipase A2 in healthy older adult males and females", Eu. J. Nutr. 50, 2011, pp. 185-196.
Neubronner, et al., "Enhanced increase of omega-3 index in response to long-term n-3 fatty acid supplementation from triacylclycerides versus ethyl esters", European Journal of Clinical Nutrition 65, 2011, pp. 247-254.
Nordgestgaard, "Nonfasting Triglycerides and Risk of Myocardial Infarction, Ischemic Heart Disease, and Death in Men and Women", Journal of American Medical Association, vol. 198, No. 3, Jul. 18, 2007, pp. 299-308.
Norweigan Scientific Committee for Food Safety, "Description of the processes in the calue chain and risk assessment of decomposition substances and oxidation products in fish oils", Opinion of Steering Committee of the Norwegian Scientific Committee for Food Safety, Doc. No. 08-504-4-final, ISBN: 978-82-8259-035-8, Oct. 19, 2011, 147 pages.
Offman, et al., "Steady-state bioavailability of prescription omega-3 on low-fat diet is significantly improved with a free fatty acid formularion compared with an ethyl ester formulartion; the ECLIPSE II study", Vascular Health and Risk Management 9, 2013, pp. 563-573.
Pedersen, et al., "The effect of marine n-3 fatty acids in different doses on plasma concentrations of Lp-PLA2 in healthy adults", Eur. J. Nutr. 48, 2009, pp. 1-5.
Pharma Marine, "Calamarine at a Glance", Version 1.2, 2011, 1 page.
Reis, et al., "Effects of Two Types of Fish Oil Supplements on Serum Lipids and Plasma Phopholipid Fatty Acids in Coronary Artery Disease", The American Journal of Cardiology 66, Nov. 15, 1990, pp. 1171-1175.
Rizos, "Association Between Omega-3 Fatty Acid Supplementation and Risk of Major Cardiovascular Disease Events", Journal of American Medical Association 10, 2012, pp. 1024-1033.
Sarwar, et al., "Triglycerides and the Risk of Coronary Heart Disease", Circulation, Epidemiology 115, 2007, pp. 450-458.
Schmidt, et al., "n-3 Polyunsaturated Fatty Acid Supplementation (Pikasol) in Men with Moderate and Severe Hypertriglyceridaemia: A Dose-Response Study", Ann. Nutr. Metab. 36, 1992, pp. 283-287.
Schmidt, "The effects of n-3 fatty acids on plasma lipids and lipoproteins and other cardiovascular risk factors in patients with hyperlipidemia", Atherosclerosis 103, 1993, pp. 107-121.
Schuchardt, et al., "Associations between Omega-3 Index increase and triacylglyceride decrease in subjects with hypertriglyceridemia in response to six month of EPA and DHA supplementation", Prostaglandins, Leukotrienes and Essential Fatty Acids 91, 2014, pp. 129-134.
Schuchardt, et al., "Bioavailability of long-chain omega-3 fatty acids", Prostaglandins, Leukotrienes and Essential Fatty Acids 89, 2013, pp. 1-8.
Schuchardt, et al., "Moderate does of EPA and DHA from re-esterified triacylglycerols but not from ethyl-esters lower fasting serum triacylglycerols in stain-treated dyslipidemic subjects: Results from a six month randomized controlled trial", Prostaglandins, Leukotrienes and Essential Fatty Acids 85, 2011, pp. 381-386.
Schwellenbach, et al., "The Triglyceride-Lowering Effects of a Modest Doe of Docosahexaenoic Acid Alone Versus in Combination with Low Dose Eixosapentaenoic Acid in Patients with Coronary Artery Disease and Elevated Triglycerides", Journal of the American College of Nutrition, vol. 25, No. 6, 2006, pp. 480-485.
Stensvold, et al., "Non-Fasting Serum Triglyceride Concentration and Mortality from Coronary Heart Disease and any Cause in Middle Aged Norwegian Women", British Medical Journal, vol. 307, Nov. 20, 1993, pp. 1318-1322.
Thompson, et al., "Lipoprotein-associates phospholipase A2 and risk of coronary disease, stroke, and mortality: collaborative analysis of 32 prospective studies", The Lancet, vol. 375, 2010, pp. 1536-1544.

(56) References Cited

OTHER PUBLICATIONS

Thomsen, et al., "Low Nonfasting Triglycerides and Reduced All-Cause Mortality: A Mendelian Randomization Study", Clinical Chemistry 60:5, 2014, pp. 737-746.

Wachira, et al., "n-3 Fatty acids affect haemostatis but do not increase the risk of bleeding: clinical observations and mechanistic insights", British Journal of Nutrition, 111, 2014, pp. 1652-1662.

Walldius, et al., "Apolipoprotein B and apolipoprotein A-I: risk indicators of coronary heart disease and targets for lipid-modifying therapy", Journal of Internal Medicine, 255, 2004, pp. 188-205.

\* cited by examiner

OMEGA-3 COMPOSITIONS, DOSAGE FORMS, AND METHODS OF USE

RELATED APPLICATIONS

This application is a continuation of International Application No. PCT/US15/34372 filed on Jun. 6, 2014 and titled "OMEGA-3 COMPOSITIONS, DOSAGE FORMS, AND METHODS OF USE" and also claims the benefit of the earlier filing date of both U.S. Provisional Application No. 62/009,145 filed on Jun. 6, 2014 and titled "OMEGA-3 COMPOSITIONS, DOSAGE FORMS, AND METHODS OF USE" and U.S. Provisional Application No. 62/019,289 filed on Jun. 30, 2014 and titled "OMEGA-3 COMPOSITIONS, DOSAGE FORMS, AND METHODS OF USE," the entire contents of these applications are hereby incorporated by reference in their entirety.

TECHNICAL FIELD

Embodiments of the invention relate generally to medicinal compositions, and more particularly to omega-3 compositions, dosage forms, and methods of use.

BACKGROUND

Mammals have only a limited ability to synthesize omega-3 fatty acids, and thus generally rely on other sources to obtain 5Z,8Z,11Z,14Z,17Z-eicosapentaenoic acid (EPA) and 4Z,7Z,10Z,13Z,16Z,19Z-docosahexaenoic acid (DHA).

Omega-3 fatty acids are associated with numerous health benefits, including protection against heart disease. Some studies have identified potential benefits for other conditions as well, including autoimmune diseases, inflammatory bowel disease, and cancer.

DETAILED DESCRIPTION

Figure 1:
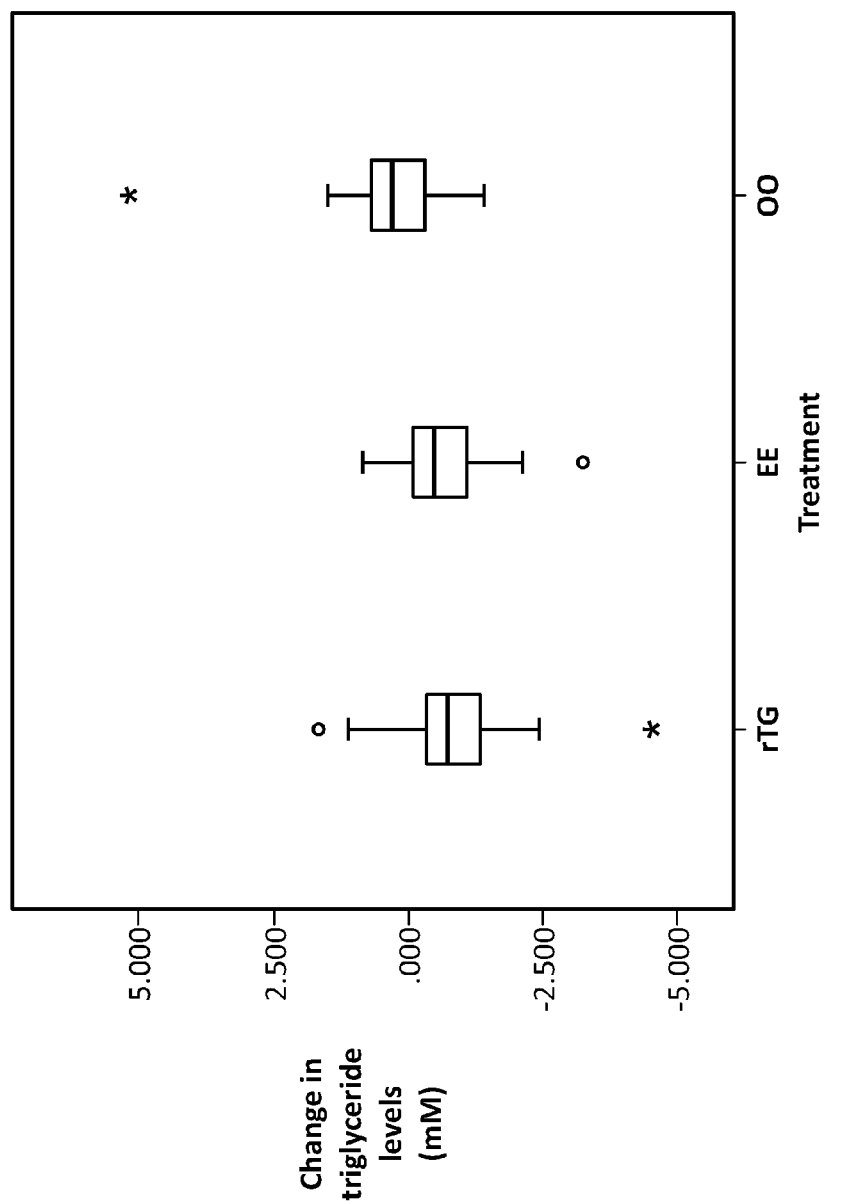
FIG. 1 is a box-and-whisker plot showing changes in blood (plasma) serum triglyceride levels during the study disclosed in Example 1.

The following detailed description of various embodiments is not intended to limit the scope of the present disclosure, but is merely representative of various embodiments. The present disclosure relates to medicinal compositions, and more particularly, to omega-3 compositions, dosage forms, and methods of use.

The term "about," when used with reference to ratios, amounts, or percentages of one or more elements of a composition, dosage form, or portion thereof, encompasses both the actual ratios, amounts, and percentages of the elements (as measured) and the ratios, amounts, and percentages after correction using standard correction methods (e.g., to compensate for the flame ionization detection response for each component). For example, a marine oil comprising fatty acids, including omega-3 polyunsaturated fatty acids (PUFAs), wherein at least about 50% of the fatty acids are triglycerides (TGs), encompasses marine oils where at least about 50% of the fatty acids, on either a corrected or uncorrected basis, are TGs.

Some compositions disclosed herein comprise a marine oil that comprises fatty acids, including omega-3 polyunsaturated fatty acids (PUFAs). In these compositions, 4Z,7Z,10Z,13Z,16Z,19Z-docosahexaenoic acid (DHA) and 5Z,8Z,11Z,14Z,17Z-eicosapentaenoic acid (EPA) comprise at least a portion of the PUFAs, and the ratio of DHA to EPA may be about 3:2 to about 4:1. For example, in some compositions, the ratio of DHA to EPA is about 5:2.

In some compositions, at least about 50% (more particularly about 55-70%) of the fatty acids are triglycerides (TGs). In some embodiments, at least about 55% of the fatty acids are TGs.

In some compositions, about 25% to about 45% of the fatty acids are diglycerides (DGs). In some compositions, about 0% to about 5% of the fatty acids are monoglycerides (MGs). In some compositions, about 5% or less (or, more particularly, about 1% or less) of the fatty acids are ethyl esters. In some compositions, about 60% of the fatty acids are PUFAs. In some compositions, at least about 55% of the fatty acids are omega-3 PUFAs. In some compositions, at least about 50% of the fatty acids are either DHA or EPA.

In some compositions, about 0% to about 35% of the fatty acids are mono-unsaturated fatty acids. In some compositions, about 0% to about 5% of the fatty acids are saturated fatty acids. In some compositions, at least about 80% of the PUFAs are DHA and EPA. In some compositions at least about 15% of the marine oil is derived from cephalopod oil. In some compositions, about 10% to about 25% of the marine oil is derived from cephalopod oil and the remainder is derived from fish oil. In some compositions about 25% to about 50% of the marine oil is derived from cephalopod oil and the remainder is derived from fish oil. In some compositions, at least about 50% of the marine oil is derived from cephalopod oil.

In some compositions, the ratio of DHA to EPA is about 5:2, about 55% to about 70% of the fatty acids are re-esterified triglycerides (rTGs), and about 25% to about 45% of the fatty acids are re-esterified diglycerides (rDGs).

In the embodiments described herein, a portion or all of the triglycerides, diglycerides, and/or monoglycerides may be re-esterified. For example, in some compositions, at least about 50% of the fatty acids are rTGs.

Some dosages forms disclosed herein comprise a marine oil comprising fatty acids, including omega-3 PUFAs, wherein DHA and EPA comprise at least a portion of the PUFAs. In such dosages forms, the amount of DHA may be at least about 450 mg and the amount of EPA may be at least about 150 mg.

In some dosage forms, the ratio of DHA to EPA may be about 3:2 to about 4:1 (e.g., about 5:2).

In some dosage forms, at least about 50% of the fatty acids are triglycerides.

In some dosage forms, at least about 50% of the fatty acids are re-esterified triglycerides.

In some dosage forms, the amount of DHA is about 450 mg to about 700 mg. In some dosage forms, the amount of EPA is about 150 mg to about 300 mg.

In some embodiments, the dosage form is a capsule, such as a liquid-filled capsule, where the liquid is a marine oil disclosed herein.

In some embodiments, the dosage form is a liquid, such as delivered in a 150 milliliter bottle. In such embodiments, the marine oil may be dispersed in a flavored carrier.

In some embodiments, the mass of the dosage form is about 1200 mg to about 1600 mg.

In some dosage forms, at least about 55% of the fatty acids are TGs. In some dosage forms, about 55% to about 70% of the fatty acids are TGs.

In some dosage forms, about 25% to about 45% of the PUFAs are DGs.

In some dosage forms, about 0% to about 5% of the fatty acids are MGs.

In some dosage forms, about 5% or less (e.g., 1% or less) of the fatty acids are ethyl esters. In some dosage forms, less than about 1% of the fatty acids are ethyl esters.

In some dosage forms, at least about 60% of the fatty acids are PUFAs.

In some dosage forms, at least about 55% of the fatty acids are omega-3 PUFAs.

In some dosage forms, at least about 50% of the fatty acids are omega-3 PUFAs.

In some dosage forms, about 0% to about 35% of the fatty acids are mono-unsaturated fatty acids.

In some dosage forms, about 0% to about 5% of the fatty acids are saturated fatty acids.

In some dosage forms, at least about 80% of the PUFAs are DHA and EPA.

In some dosage forms, at least about 15% (e.g., at least about 50%) of the marine oil is derived from cephalopod oil. In some dosage forms, about 10% to about 25% of the marine oil is derived from cephalopod oil and the remainder is derived from fish oil. In some dosage forms, about 25% to about 50% of the marine oil is derived from cephalopod oil and the remainder is derived from fish oil.

The foregoing compositions and dosage forms (and other compositions and dosage forms disclosed herein) may be used in methods of treatment. For example, the present disclosure encompasses a method of reducing the risk of mortality in a subject comprising administering a composition or dosage form disclosed herein.

The present disclosure encompasses a method of extending the life of a subject comprising administering a composition or dosage form disclosed herein.

The present disclosure encompasses a method of reducing the risk of coronary heart disease (CHD) in a subject comprising administering a composition or dosage form disclosed herein.

The present disclosure encompasses a method of reducing the risk of sudden cardiac death (SCD) in a subject comprising administering a composition or dosage form disclosed herein.

The present disclosure encompasses a method of reducing the risk of cardiac arrest in a subject comprising administering a composition or dosage form disclosed herein.

The present disclosure encompasses a method of reducing non-fasting triglyceride levels in a subject's blood comprising administering a composition or dosage form disclosed herein.

The present disclosure encompasses a method of reducing fasting triglyceride levels in a subject's blood comprising administering a composition or dosage form disclosed herein.

The present disclosure encompasses a method of increasing the omega-3 index in red bloods cells of a subject comprising administering a composition or dosage form disclosed herein. Some of such embodiments further comprise identifying a subject with less than an average of about 8% EPA and/or DHA in the red blood cells of the subject.

The present disclosure encompasses a method of reducing the resting heart rate of a subject comprising administering a composition or dosage form disclosed herein.

The present disclosure encompasses a method of increasing high-density lipoprotein cholesterol (HDL-c) in a subject comprising administering a composition or dosage form disclosed herein.

The present disclosure encompasses a method of reducing non-high-density-lipoprotein cholesterol (non-HDL-c) in a subject comprising administering a composition or dosage form disclosed herein.

The present disclosure encompasses a method of reducing total cholesterol in a subject comprising administering a composition or dosage form disclosed herein.

The present disclosure encompasses a method of reducing apolipoprotein B (Apo-B) in a subject's blood comprising administering a composition or dosage form disclosed herein.

The present disclosure encompasses a method of reducing systolic blood pressure in a subject comprising administering a composition or dosage form disclosed herein.

The present disclosure encompasses a method of reducing diastolic blood pressure in a subject comprising administering a composition or dosage form disclosed herein.

The present disclosure encompasses a method of treating hypertriglyceridemia in a subject comprising administering a composition or dosage form disclosed herein. More particularly, some methods of treating hypertriglyceridemia using a composition or dosage form disclosed herein comprise identifying a subject with hypertriglyceridemia.

In some embodiments of each of the methods of treatment disclosed herein, the dose of DHA is at least about 1800 mg/day (e.g., about 1800 mg/day to about 2400 mg/day). In some such embodiments, the dose of DHA is at least about 1800 mg/day and the dose of EPA is about 700 mg/day to about 1000 mg/day. In some of such embodiments, the dose of DHA is about 900 mg to about 1200 mg, twice a day, and the dose of EPA is about 350 mg to about 500 mg, twice a day.

Some embodiments of each of the methods or treatment disclosed herein may reduce apolipoprotein B (Apo-B) in a subject's blood and increase apolipoprotein A-1 (Apo-A-1) in a subject's blood, thereby decreasing the ratio of Apo-B to Apo-A-1.

Compositions and precursors of compositions disclosed herein may be manufactured by any suitable method. For example, some compositions may be manufactured, at least in part, from crude fish oil or crude cephalopod (e.g., squid) oil. The following methods and/or steps for processing fish and/or squid oil are illustrative, and are not meant to limit the scope of this disclosure.

In some methods, crude squid or fish oil may be deacidified by treatment with one or more bases such as NaOH, thereby reducing oil acidity. More particularly, in some methods, aqueous NaOH is added to the crude fish or squid oil, and the crude oil is then isolated by one or more of aqueous/organic phase separation and distillation. In some methods, after addition of a base, volatile material (e.g., free fatty acid) may be stripped by means of a stripping gas (e.g., steam at a high temperature and low pressure).

In some methods, ethyl esters may be produced from the fish or squid oil by chemical reaction with the deacidified fish or squid oil. For example, the deacidified fish or squid oil may be reacted with ethanol (e.g., through a sodium ethoxide-catalyzed transesterification reaction) to form ethyl esters. Additionally or alternatively, in some embodiments, microbial lipases may be used for such a transesterification reaction.

In some methods, the resulting ethyl esters may then be concentrated by molecular distillation. In some methods, the ethyl esters may additionally or alternatively be concentrated through urea complexation. In some urea complexation procedures, ethyl esters are mixed with an ethanolic solution of urea with moderate heating. The mixture is then allowed to cool, causing the urea to crystallize. Because urea crystallizes into a hexagonal structure with channels of appropriate size to accommodate straight-chain saturated fatty acids, fatty acids with a low degree of unsaturation remain complexed with the urea, while fatty acids with a higher degree of saturation (e.g., DHA and EPA) are separated in the solution and may be isolated by filtration.

A method of processing crude fish or squid oil may comprise re-esterification of ethyl ester fatty acids to produce a re-esterified triglyceride. For example, ethyl esters may be enzymatically converted to triglycerides.

In some methods, fish or squid oil (either in ethyl ester form or as a re-esterified triglyceride) may, at some point, undergo a bleaching process. For example, the oil may be heated (e.g., to approximately 80-85° C.) and mixed with activated bleaching clay and/or activated carbon. The bleaching clay, activated carbon, or other beaching agent may adsorb soaps, sulfur-containing compounds, trace metals, pigments, and/or other components.

In some embodiments, fish or squid oil may be deodorized to remove, inter alia, free fatty acids, aldehydes, and ketones or other compounds or materials. In the absence of such deodorization, the fish oil may have objectionable flavor and/or smell characteristics. In some embodiments, volatile material is stripped by means of a stripping gas (e.g., steam at high temperature and low pressure).

Some compositions disclosed herein comprise a mixture of oils from distinct sources. For example, some compositions or dosage forms may comprise cephalopod oil and/or fish oil. In some embodiments, cephalopod oil may be combined with fish oil. In some circumstances, the oils may be combined in large containers and that will be used to fill smaller containers (e.g., nitrogen-flushed bottles for individual sale to consumers). Further, in some embodiments, antioxidants, flavorings, tocopherol, or other additives may be added prior to sealing the containers for distribution to end users.

It should be understood that for some embodiments only a portion of the processing steps disclosed above may be performed. Additionally, some compositions or dosage forms may not be processed by the methods described above, but by alternative processes known in the art. Also, some compositions or dosage forms may be processed by blending already-purified oils.

Some embodiments of the compositions and dosage forms disclosed herein comprise re-esterified triglycerides (rTGs), including re-esterified EPA and DHA. rTGs may have advantages in therapeutic settings relative to other fatty acids, such as the ethyl ester forms of EPA and DHA. For example, as shown in Example 1 below, the triglyceride levels of a group receiving a composition with re-esterified triglycerides were reduced to a greater extent than the triglyceride levels of a group that received ethyl ester forms of EPA and DHA. Further, the group receiving a composition with re-esterified EPA and DHA had a lower heart rate, a lower hazard ratio, lower systolic and diastolic blood pressure, a higher omega-3 index, increased HDL-c levels, lower non-HDL-c levels, and lower cholesterol levels relative to the group that received ethyl ester forms of EPA and DHA.

Compositions and dosage forms comprising a relatively high ratio of DHA to EPA may have one or more advantages relative to compositions that have a lower ratio of DHA to EPA. For example, as shown in Example 1 below, patients who received about 5:2 DHA:EPA as compared to patients who received about 4:5 DHA:EPA (at comparable total omega-3 PUFA amounts) had reduced triglyceride levels, lower heart rate, decreased blood pressure, and an increased omega-3 index.

Example 1

One hundred and nineteen individuals who had been diagnosed with moderate fasting hypertriglyceridemia (i.e., 150 mg triglyceride per dL of blood plasma (1.7 mM) to 500 mg triglyceride per dL of blood plasma (5.65 mM)) were recruited to investigate the response of such individuals to three different lipophilic combinations over an eight-week period.

The 119 individuals (median age of 64) were randomly assigned to three separate groups in a 1:1:1 ratio. The first group, which is referred to herein as the re-esterified triglyceride (rTG) group, was prescribed 5.5 g of LIPOMAR™ per day (two 1.375 g capsules taken twice per day). The 5.5 g of prescribed LIPOMAR™ included 767 mg EPA and 1930 mg DHA (i.e., 2696 mg of combined EPA and DHA). The oil of the LIPOMAR™ capsules was a blend of refined and re-esterified squid and fish oils. The second group, which is referred to herein that the ethyl ester (EE) group, was prescribed 4.0 g of LOVAZA™ (two 1.0 mg capsules taken twice per day). The 4.0 g of prescribed LOVAZA™ included 1702 mg EPA and 1382 mg DHA in ethyl ester form (i.e., 3085 mg of combined EPA and DHA). The third group, referred to herein as the placebo group, received 4.0 g of olive oil (OO) per day (two 1.0 mg capsules taken twice per day).

At the beginning of the study, each individual's resting heart rate and blood pressure were measured. Additionally, one or more blood samples of each patient was taken and used to assess the concentration and/or ratio of blood components. For example, the patient's blood was tested to determine non-fasting triglyceride levels, cholesterol levels, the omega-3 index of red blood cell membranes, and the concentrations and/or ratios of various proteins and lipoproteins found in the blood. Other tests on the blood plasma were also conducted. Table 1 provides a summary of the characteristics of those in each experimental arm of the study.

TABLE 1

| | Re-esterified Triglyceride | Ethyl ester | Olive oil (placebo) |
|---|---|---|---|
| General characteristics | | | |
| Number of participants/group | N = 39 | N = 40 | N = 40 |
| Average age | 63.3 | 60.4 | 63.6 |
| Number of male participants | 36 (92.3)[1] | 26 (65.0) | 32 (80.0) |
| BMI (mean) | 29 | 28 | 29 |

TABLE 1-continued

| | Re-esterified Triglyceride | Ethyl ester | Olive oil (placebo) |
|---|---|---|---|
| Average weight of female (kg) | 82.1 | 71.1 | 81.8 |
| Range of female weight (kg) | 68-98 | 54-86 | 55-96 |
| Average weight of male (kg) | 93.1 | 89.8 | 90.4 |
| Range of male weight (kg) | 75-120 | 71-117 | 72-118 |
| History (self-declared) | | | |
| Cardiovascular disease | 30 (76.9) | 30 (75.0) | 32 (80.0) |
| Dyslipidæmi | 30 (76.9) | 35 (87.5) | 30 (75.0) |
| Hypertension | 22 (56.4) | 19 (47.5) | 20 (50.0) |
| Diabetes Mellitus Type II | 5 (12.8) | 6 (15.0) | 8 (20.0) |
| Psychiatric disorder | 1 (2.6) | 2 (5.0) | 1 (2.5) |
| Therapy | | | |
| Statin therapy users | 30 (76.9) | 29 (72.5) | 29 (72.5) |
| Ezetemibe users | 3 (7.7) | 5 (12.5) | 2 (5.0) |
| Hypertension therapy users | 27 (69.2) | 26 (65) | 30 (75.0) |
| Psychopharmaca | 3 (7.7) | 5 (12.5) | 2 (5.0) |
| Blood pressure (average) | | | |
| Systolic (mmHg) | 145 | 141 | 145 |
| Diastolic (mmHg) | 84 | 83 | 85 |
| Heart rate (average # of beats/min) | 67 | 63 | 65 |
| Lipid values (average) | | | |
| Cholesterol (mg/dL) | 247 | 240 | 218 |
| HDL (mg/dL) | 40.2 | 42.9 | 44.4 |
| Non-HDL (mg/dL) | 141.3 | 146.7 | 145.9 |
| Triglyceride (mg/dL) | 247 | 240 | 218 |
| Omega-3 index (%) | 6.7 | 6.4 | 6.2 |

[1]Numbers enclosed within parentheses denote the percentage of participants in each group that fall within the relevant category.

After four and eight weeks of treatment, the individuals in each group returned, and the measurements and tests performed at the beginning of the study were repeated. A summary of these results is set forth in the text below, and the tables and figures referenced therein.

Figure 2:
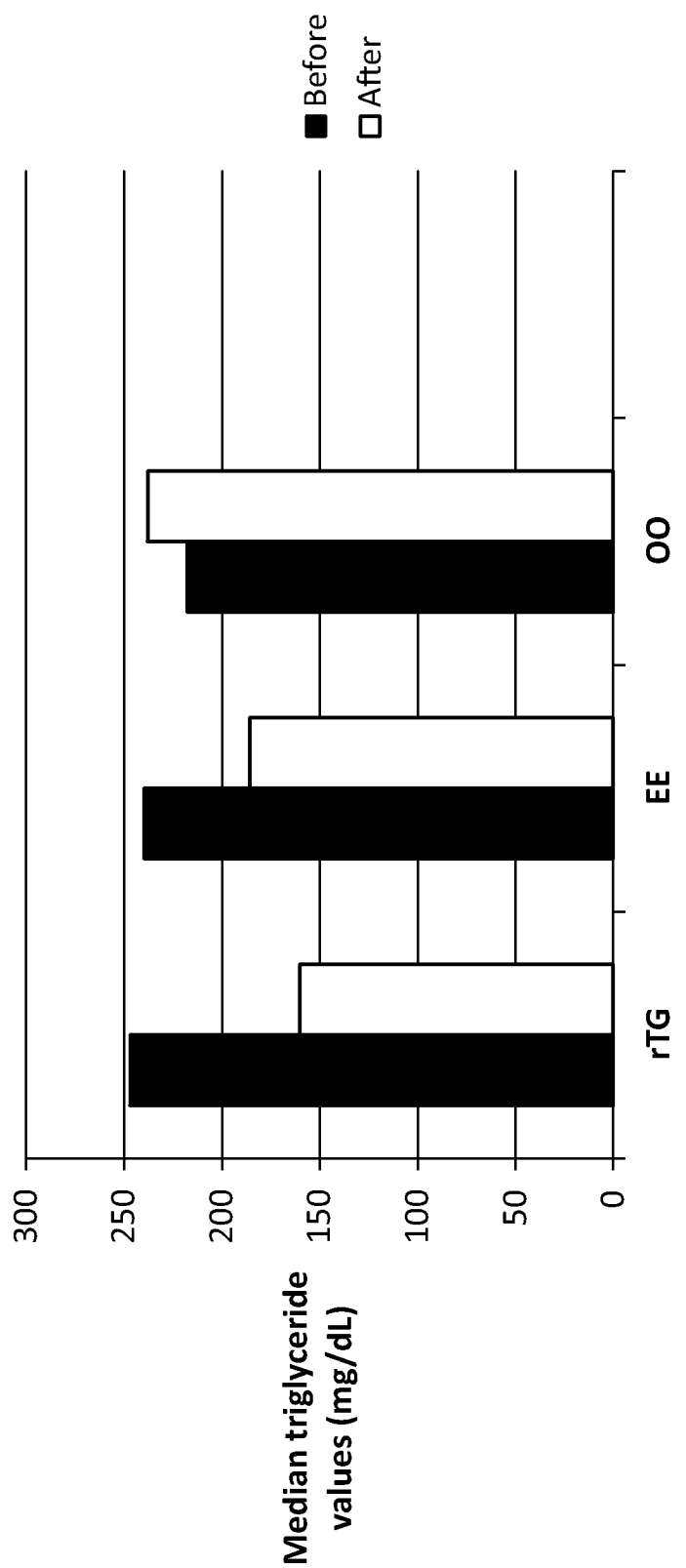
FIG. 2 is a bar graph of median non-fasting plasma triglyceride levels as measured at the beginning and at the end of the study disclosed in Example 1.
Figure 3:
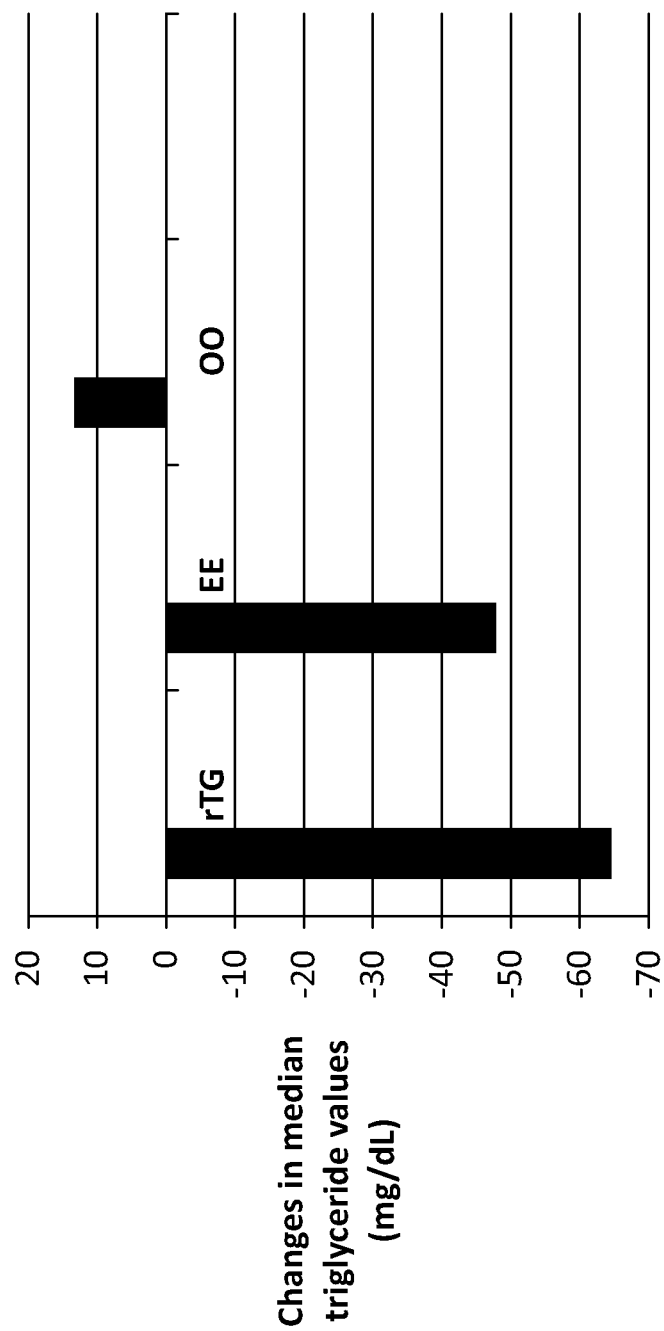
FIG. 3 is a bar graph depicting changes in median plasma non-fasting triglyceride levels as measured at the beginning and at the end of the study disclosed in Example 1.

FIGS. 1-3 provide graphical depictions of data related to changes in plasma triglyceride levels in each arm of the study. More particularly, FIG. 1 provides a box-and-whisker plot depicting, within each group, changes in blood plasma triglyceride levels between baseline levels measured at the beginning of the study and blood plasma triglyceride levels measured at the conclusion of the study. The box-and-whisker plot shows the median, upper and lower quartile, and maximum and minimum values (excluding outliers). Outlier data are depicted with circles or asterisks.

FIG. 2 provides a bar graph of median non-fasting plasma triglyceride levels (mg/dL) as measured at the beginning of the study (i.e., baseline levels) and at the conclusion of the study. FIG. 3 depicts changes in median non-fasting plasma triglyceride levels (mg/dL) as measured at the beginning of the study relative to median non-fasting plasma triglyceride levels as measured at the conclusion of the study. As depicted in these figures, the median non-fasting triglyceride levels for the rTG arm and the EE arm of the study were lowered from baseline levels (from 2.79±1.12 mM to 1.81±0.82 mM for the rTG arm and from 2.70±1.39 mM to 2.10±1.23 mM for the EE arm), while the median non-fasting triglyceride level for the placebo arm did not decrease (changing from 2.46±1.38 mM to 2.69±1.62 mM). The decrease in plasma triglyceride levels for the rTG and EE arms relative to baseline levels was statistically significant (p-values<0.001). The decrease in plasma triglyceride levels in both the rTG and EE arms was also statistically significant when compared with the placebo group receiving olive oil (p-values<0.001). Changes in triglyceride levels within the placebo group were not statistically significant (p-value=0.52).

Figure 4:
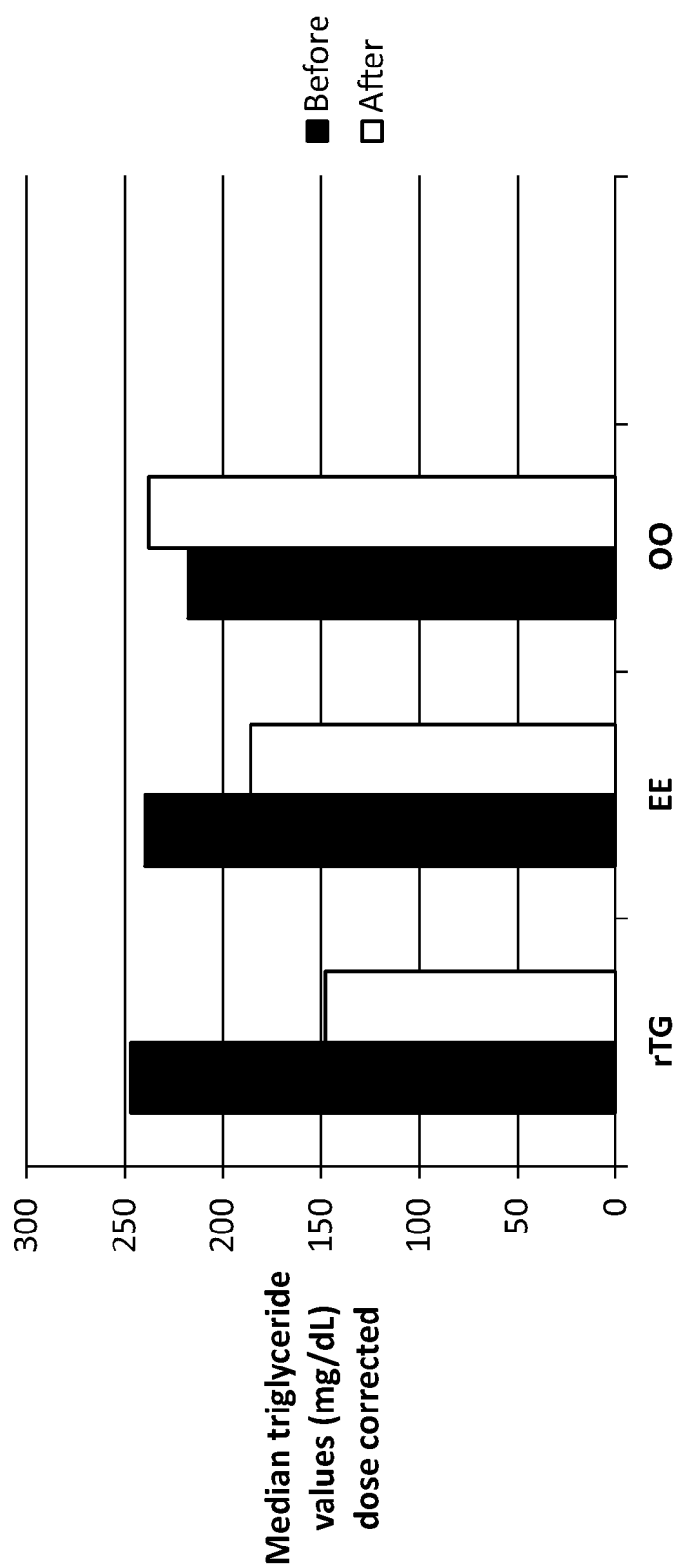
FIG. 4 is a bar graph of median corrected non-fasting plasma triglyceride levels as measured at the beginning and at the end of the study disclosed in Example 1.
Figure 5:
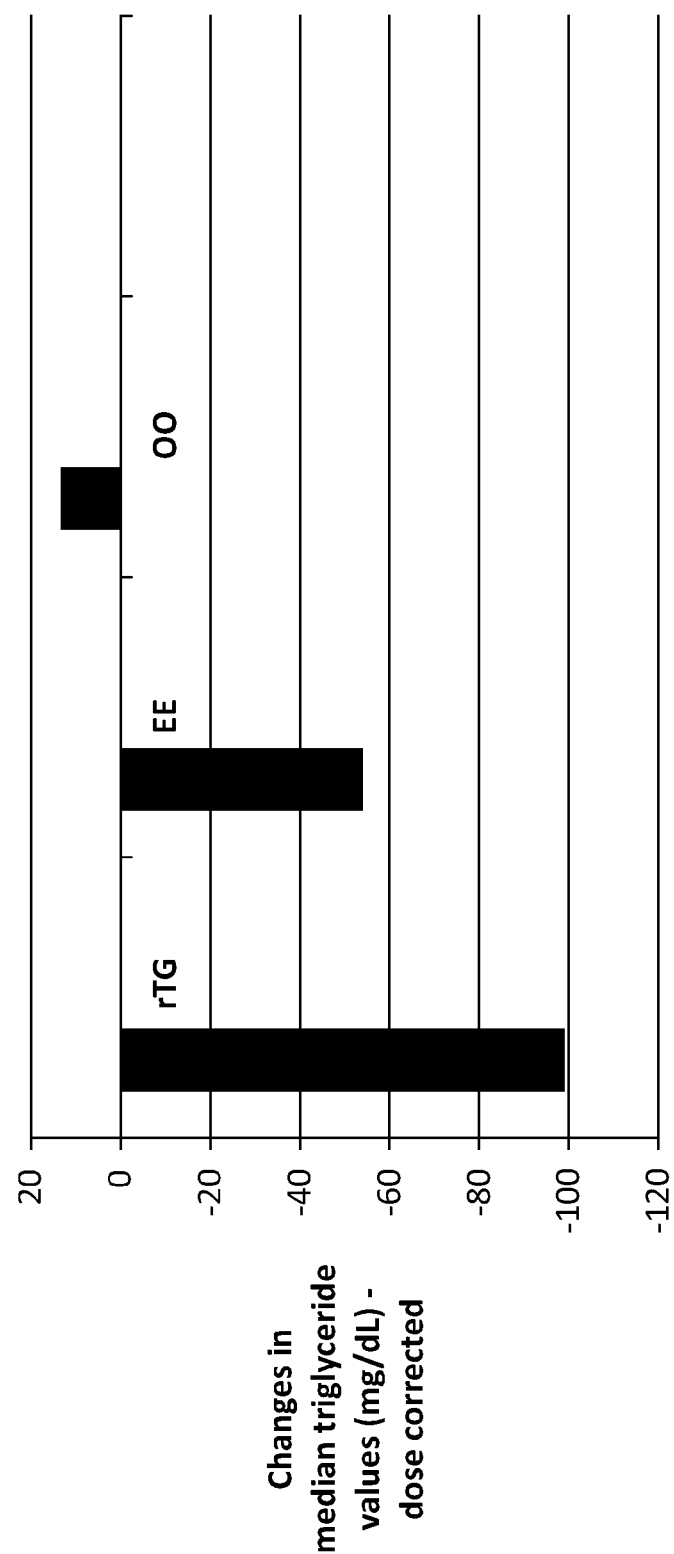
FIG. 5 is a bar graph depicting changes in median corrected plasma non-fasting triglyceride levels as measured at the beginning and at the end of the study disclosed in Example 1.

The total amount (by weight) of combined EPA and DHA differs in the two experimental arms of the study. More particularly, the ethyl ester treatment arm (i.e., LOVAZA) receives 14% more combined EPA and DHA by weight than the group receiving re-esterified triglyceride. FIGS. 4 and 5 are analogous to FIGS. 2 and 3, but correct for this difference in total amount of supplied EPA and DHA. As shown in these figures, the decrease in median plasma triglyceride levels for the rTG arm of the study is even more pronounced when the data are corrected to account for the difference in the total amount of combined EPA and DHA by weight.

Figure 6:
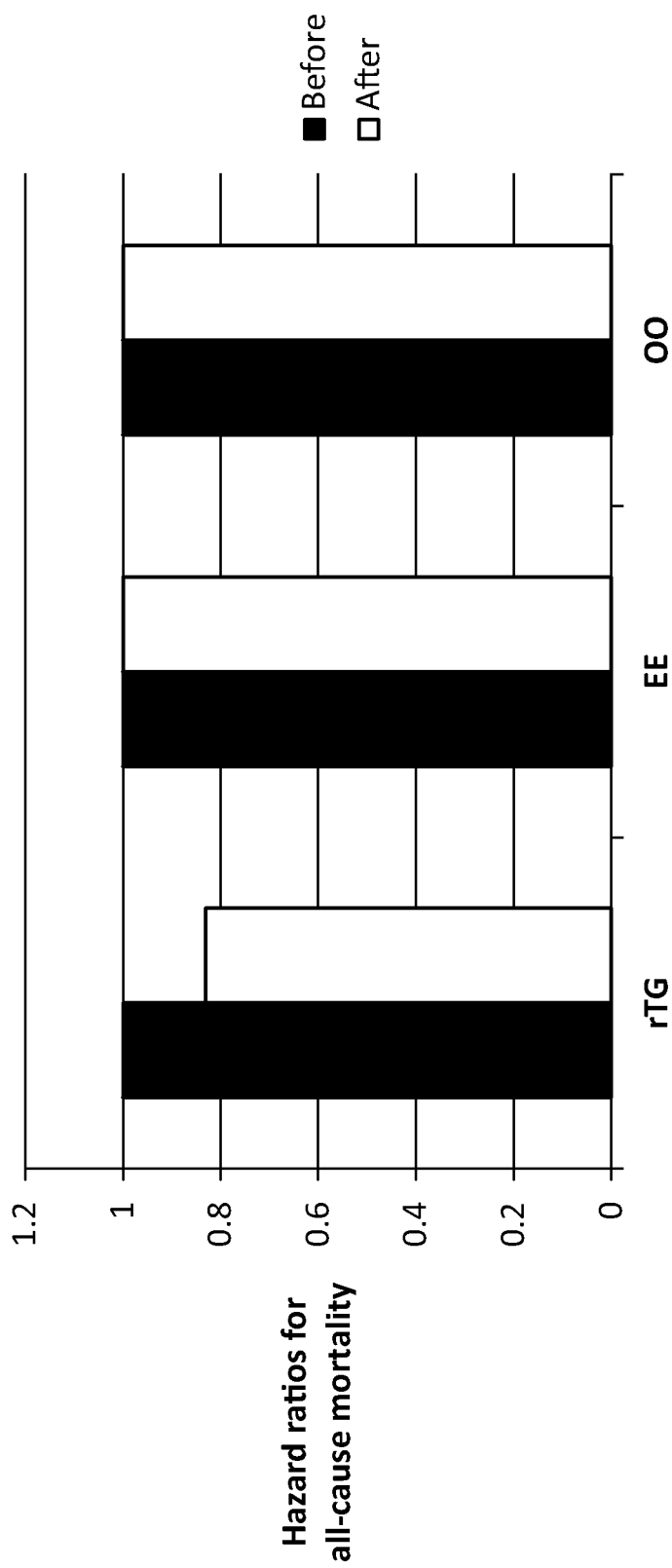
FIG. 6 is a bar graph providing hazard ratios for all-cause mortality in each experimental arm of the study disclosed in Example 1.

FIG. 6 is a bar graph providing hazard ratios for all-cause mortality in each experimental arm of the study. The hazard ratios are determined and defined as set forth in Thomsen et al., *Low Nonfasting Triglycerides and Reduced All-Cause Mortality: A Mendelian Randomization Study*, 60 Clin. Chem 737-46 (2014), which is incorporated herein by reference. The hazard ratio remained constant throughout the study in both the EE group and the placebo group. However, the hazard ratio for those in the rTG group was lowered at the conclusion of the study relative to the hazard ratio at the beginning of the study.

Figure 7:
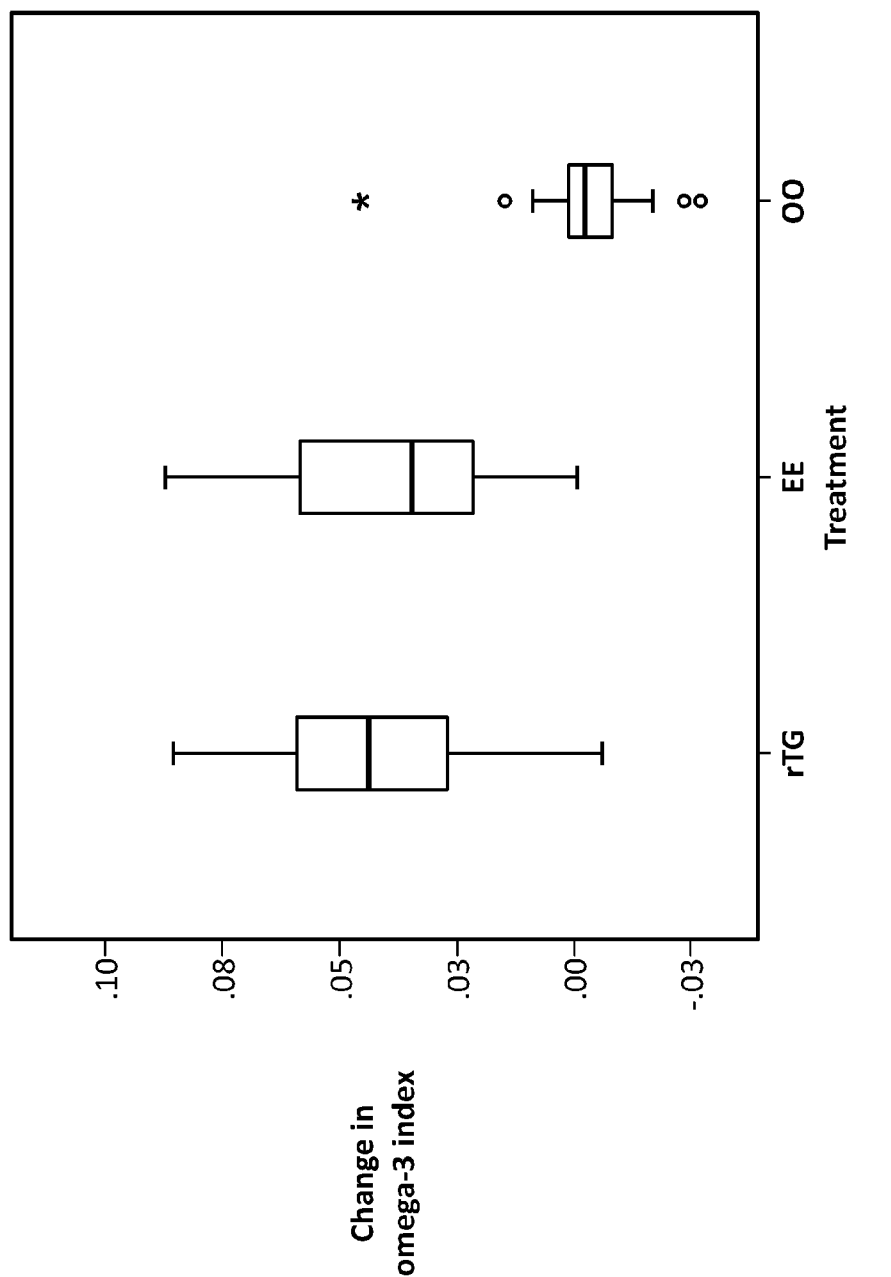
FIG. 7 is a box-and-whisker plot of changes in omega-3 index over the course of the study disclosed in Example 1.
Figure 8:
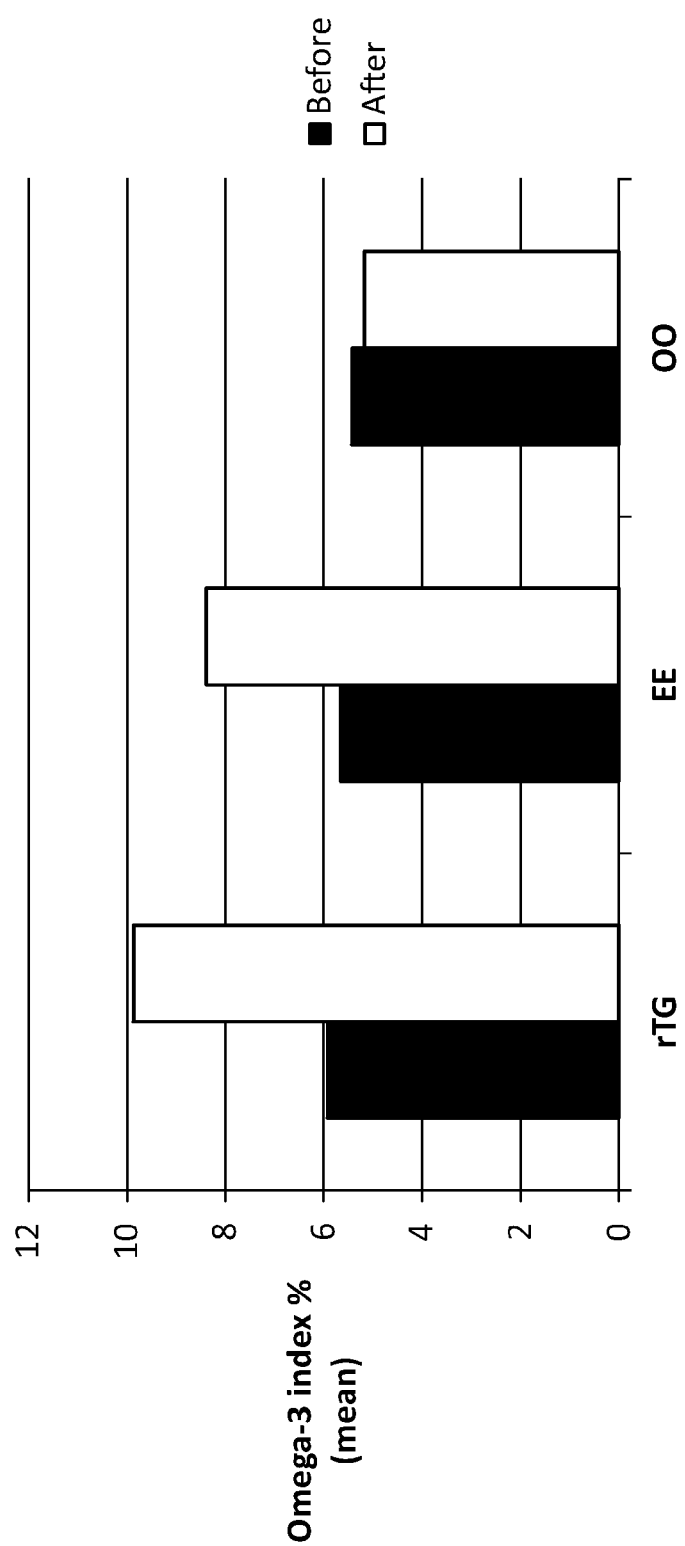
FIG. 8 is a bar graph depicting the mean omega-3 index for each arm of the study disclosed in Example 1, both before and after treatment.
Figure 9:
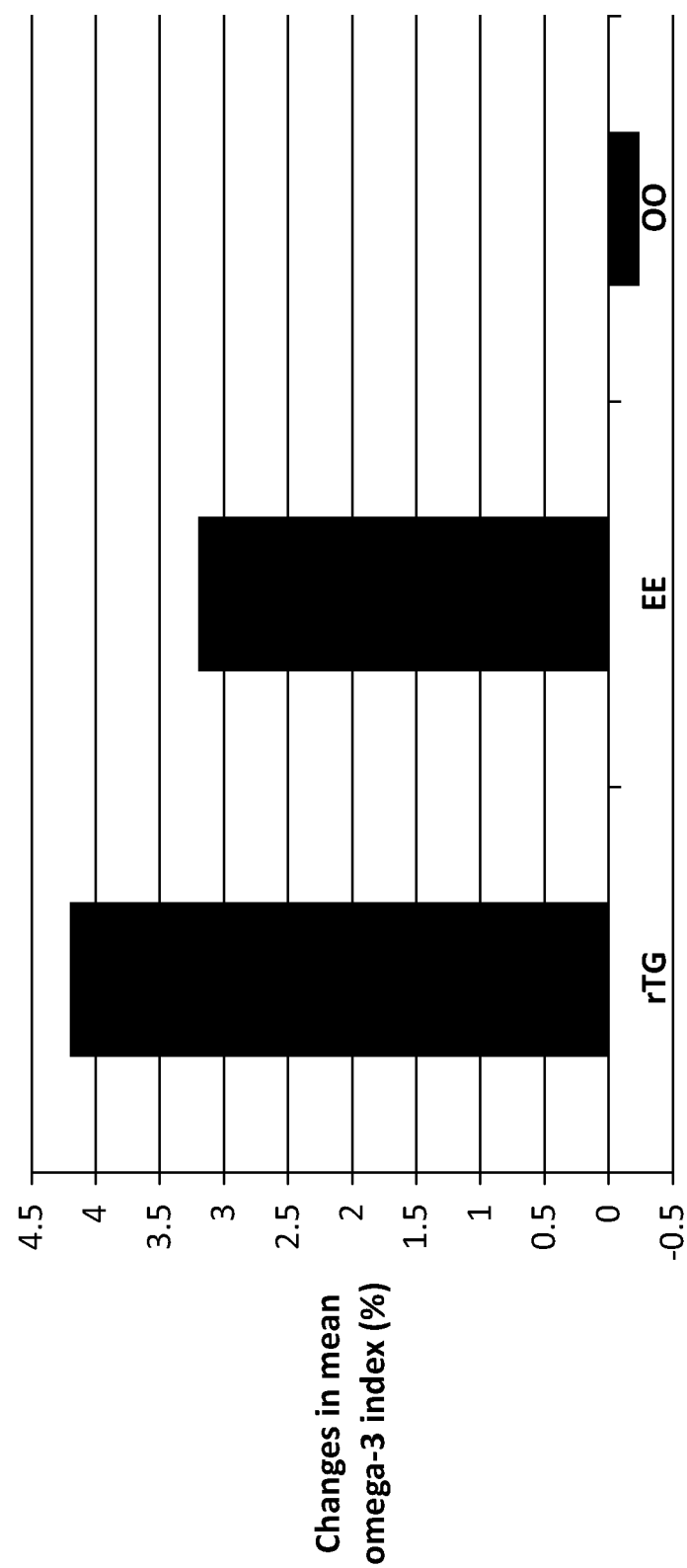
FIG. 9 is a bar graph depicting changes in omega-3 index over the course of the study disclosed in Example 1.

FIGS. 7, 8, and 9 provide graphical depictions of data related to the changes in the omega-3 index of members of the study population. The omega-3 index is defined as the ratio of the combined number of EPA and DHA fatty acids in the measured erythrocyte membranes relative to the total number of all fatty acids (including EPA and DHA) in the measured erythrocyte membranes. The ratio is expressed either as a ratio or a percentage. FIG. 7 provides a box-and-whisker plot of the changes in omega-3 index between baseline levels measured at the beginning of the study and levels measured at the conclusion of the study. The box-and-whisker plot shows the median, upper and lower quartile, and maximum and minimum values (excluding outliers). There were no outliers in the rTG and ethyl ester treatment arms. The four outliers of the control group are depicted with circles and an asterisk in the corresponding box plot. As shown in FIG. 7, the omega-3 index of those in the rTG and EE treatment arms generally increased, while the omega-3 index of those in the placebo (olive oil) group, generally did not change.

FIG. 8 depicts the mean omega-3 index for each arm of the study both before treatment and at the conclusion of the treatment period. FIG. 9 depicts changes in the mean omega-3 index across the course of the study, or stated another way, FIG. 9 depicts the difference between the values shown for each of the three columns in FIG. 8. Thus, for example, as shown in these figures, the mean omega-3 index in the rTG and EE treatment arms increased relative to both the placebo group and to baseline levels within each group. The increase in omega-3 index values in both the rTG and EE treatment arms was statistically significant relative to both the placebo group and baseline values (p-values<0.001). The increase in omega-3 index values for the rTG group relative to the EE group, as depicted in these figures, was not statistically significant. Additionally, changes in the omega-3 index in the placebo group relative to baseline values were not statistically significant.

Figure 10:
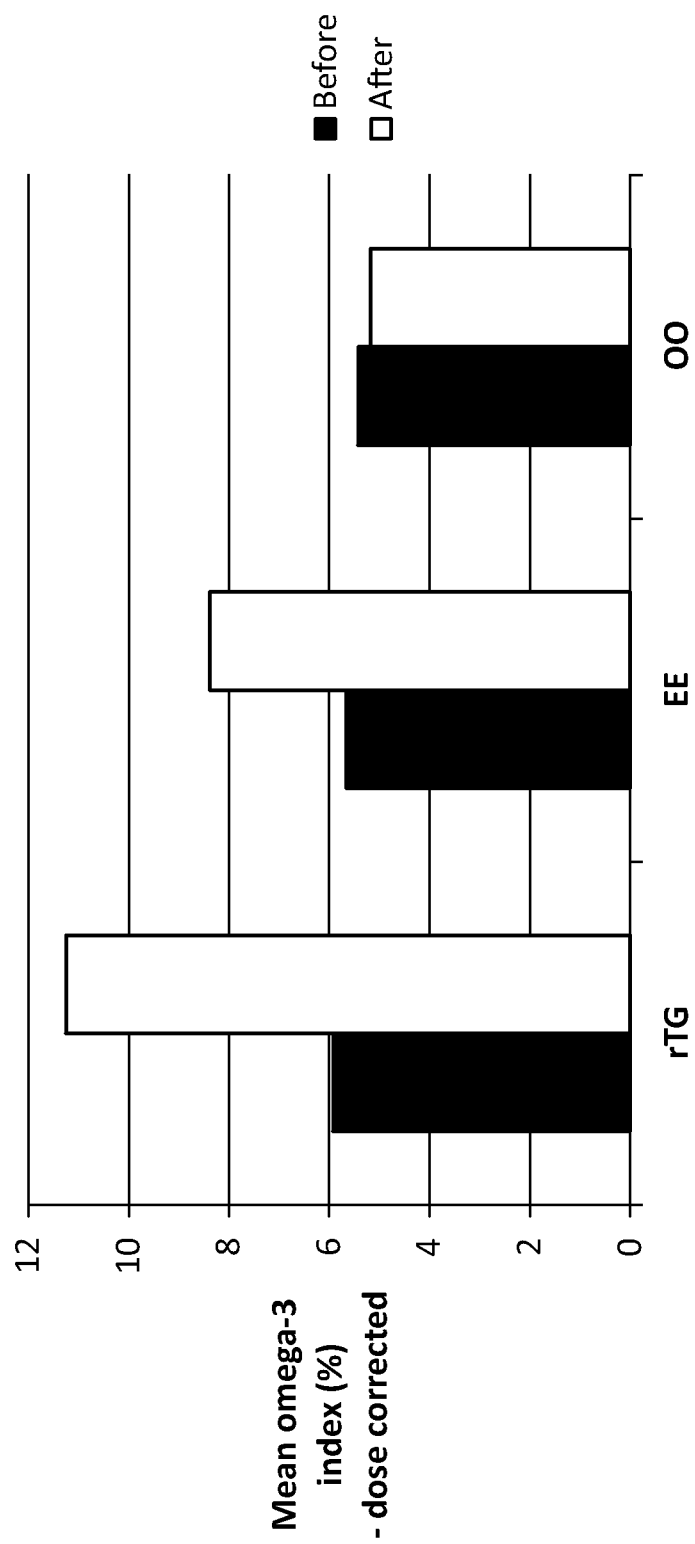
FIG. 10 is the bar graph depicting the mean dose-corrected omega-3 index for each arm of the study disclosed in Example 1, both before and after treatment.
Figure 11:
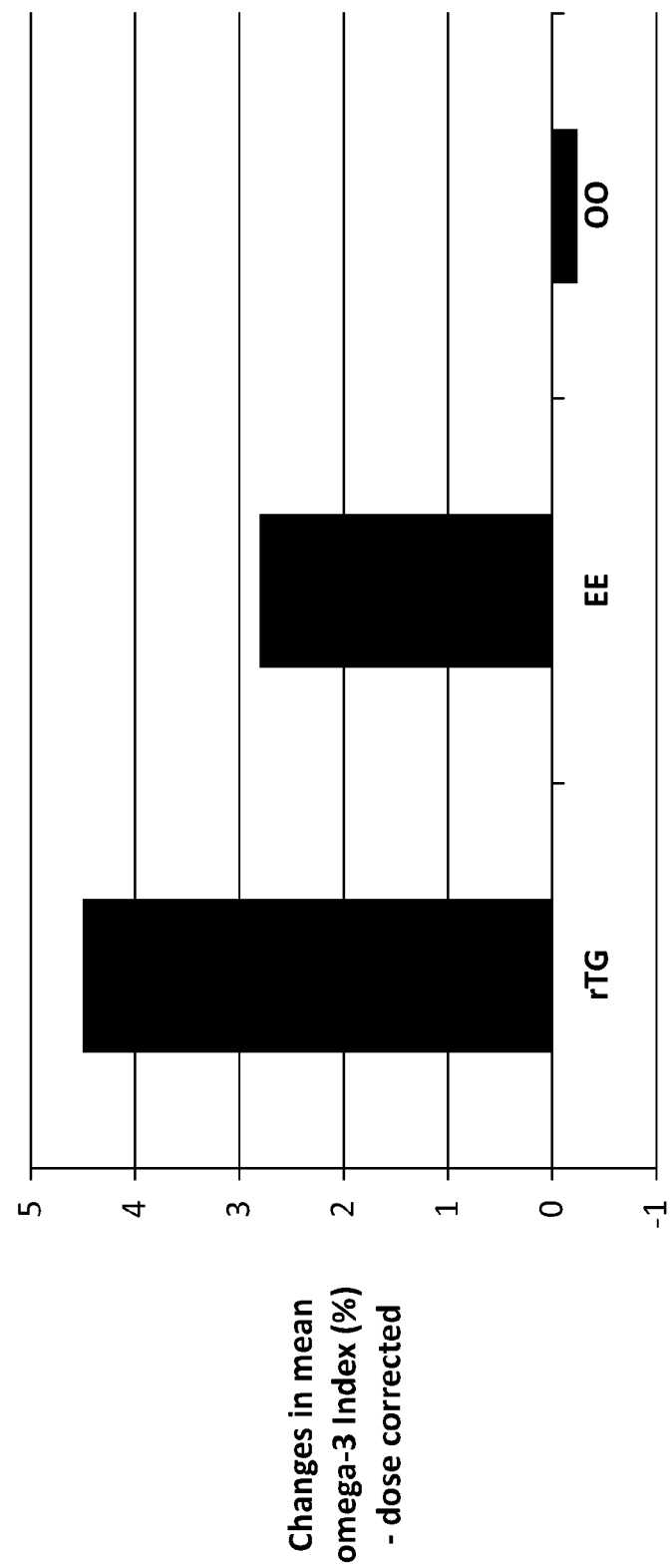
FIG. 11 is a bar graph depicting dose-corrected changes in omega-3 index over the course of the study disclosed in Example 1.

FIGS. 10 and 11 are analogous to FIGS. 8 and 9, but corrected for the total amount of EPA and DHA. As shown in these figures, the increase in mean omega-3 index values relative to baseline values is even more pronounced when the data are corrected to account for the different in the total amount of combined EPA and DHA (by weight) in treatment arms.

Figure 12:
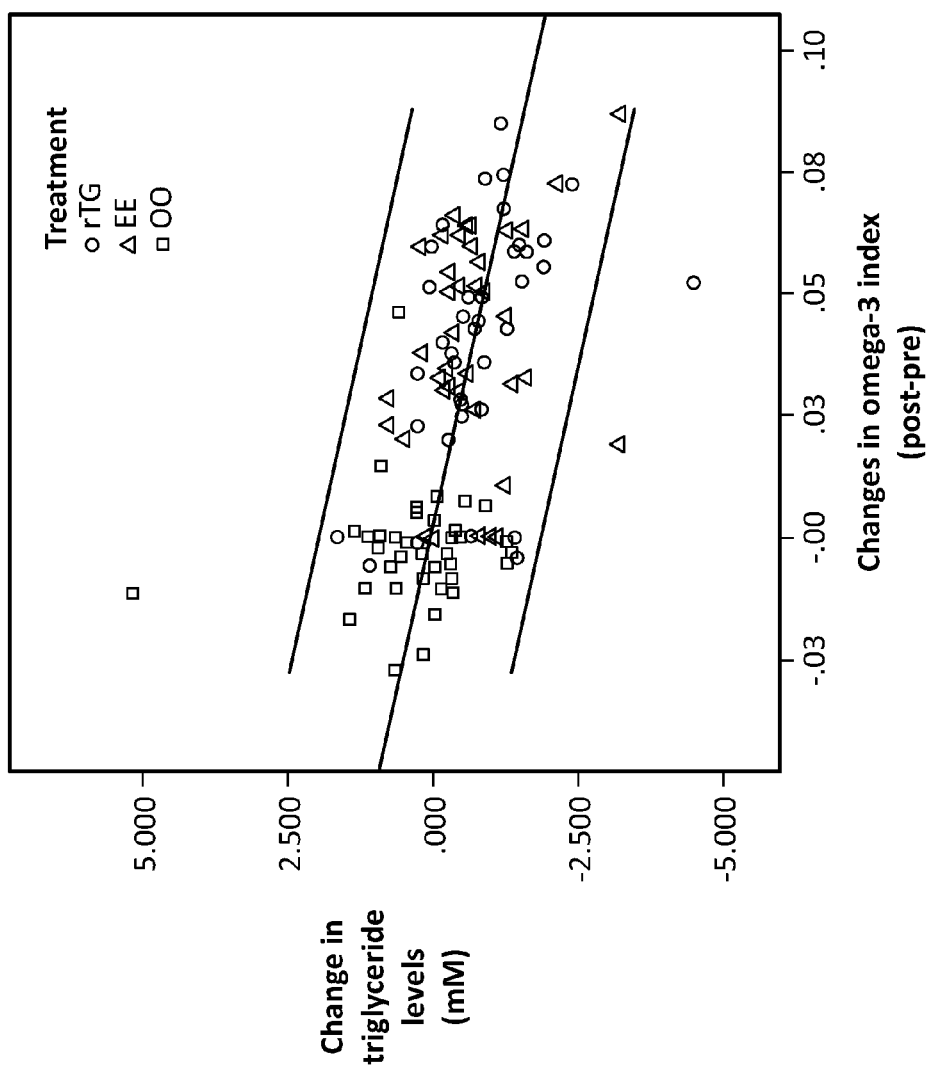
FIG. 12 is a scatter plot of the change in triglyceride levels over the course of the study disclosed in Example 1, and the change in omega-3 index observed over the course of the same study.

FIG. 12 provides a scatter plot depicting the difference between plasma triglyceride levels (mg/dL) measured at the end of the study from triglyceride levels measured at the beginning of the study (i.e., baseline levels) on the y-axis, and the difference in omega-3 index (i.e., omega-3 index levels at the conclusion of the study minus baseline omega-3 index levels measured at the beginning of the study) on the x-axis. As is evidenced by the negative slope of the best-fit line, this plot shows a negative correlation between these two variables ($R^2$ value=0.233)

Figure 13:
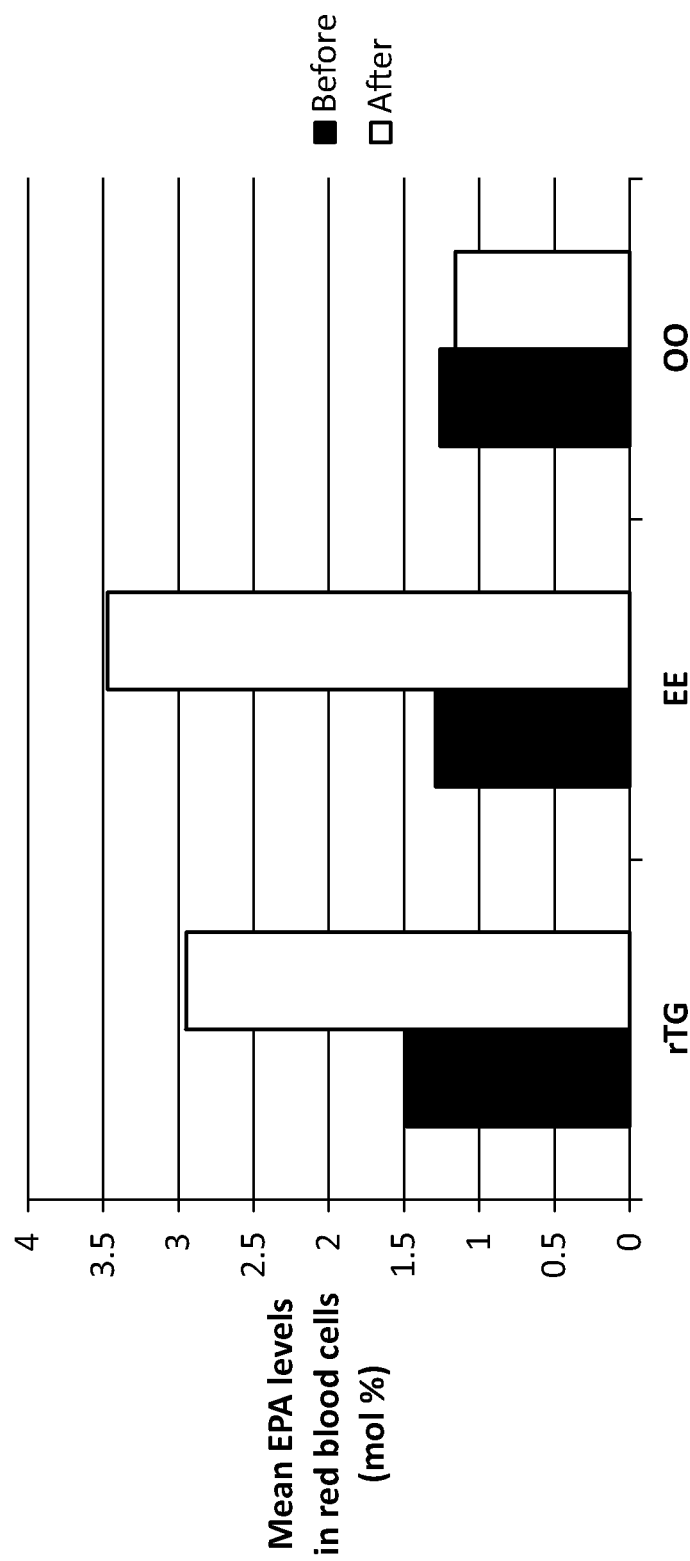
FIG. 13 is a bar graph depicting mean EPA levels in red blood cells at the beginning and at the conclusion of the study disclosed in Example 1.

FIG. 13 provides a bar graph depicting mean EPA levels (mol %) in red blood cells at the beginning of the study and at the conclusion of the study. As depicted in FIG. 13, mean EPA concentrations increased in both the rTG and EE treatment arms across the course of the study, while the mean EPA concentration of the placebo group did not increase. The increase in EPA concentrations for both treatment groups was statistically significant relative to baseline levels (p-value<0.001). The increase in EPA concentration in the EE arm was significantly greater than the increase in EPA concentrations in the rTG group (p-value<0.043). Changes in the placebo group were not statistically significant.

Figure 14:
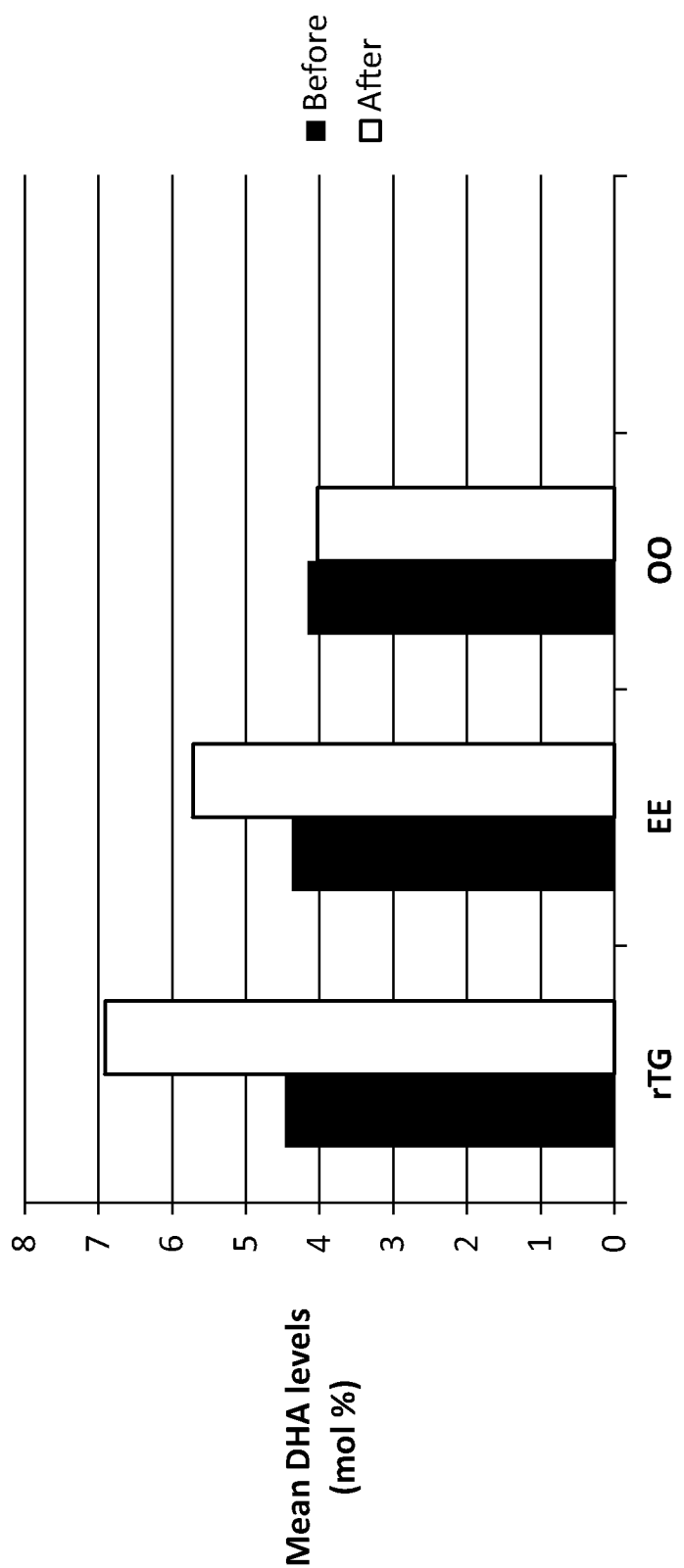
FIG. 14 is a bar graph depicting mean DHA levels in red blood cells at the beginning and at the conclusion of the study disclosed in Example 1.

FIG. 14 provides a bar graph depicting mean DHA levels (mol %) in red blood cells before and after treatment. As depicted in FIG. 14, the mean DHA concentrations increased in both the rTG and EE treatment arms across the course of the study, while the mean DHA concentration in the control group did not increase. The increase in DHA concentrations for both treatment groups was statistically significant relative to baseline levels (p-values<0.001). The increase in DHA concentration in the rTG arm was significantly greater than the increase DHA concentration in the EE arm (p-value<0.001). Changes in the olive oil placebo group were not statistically significant.

Figure 15:
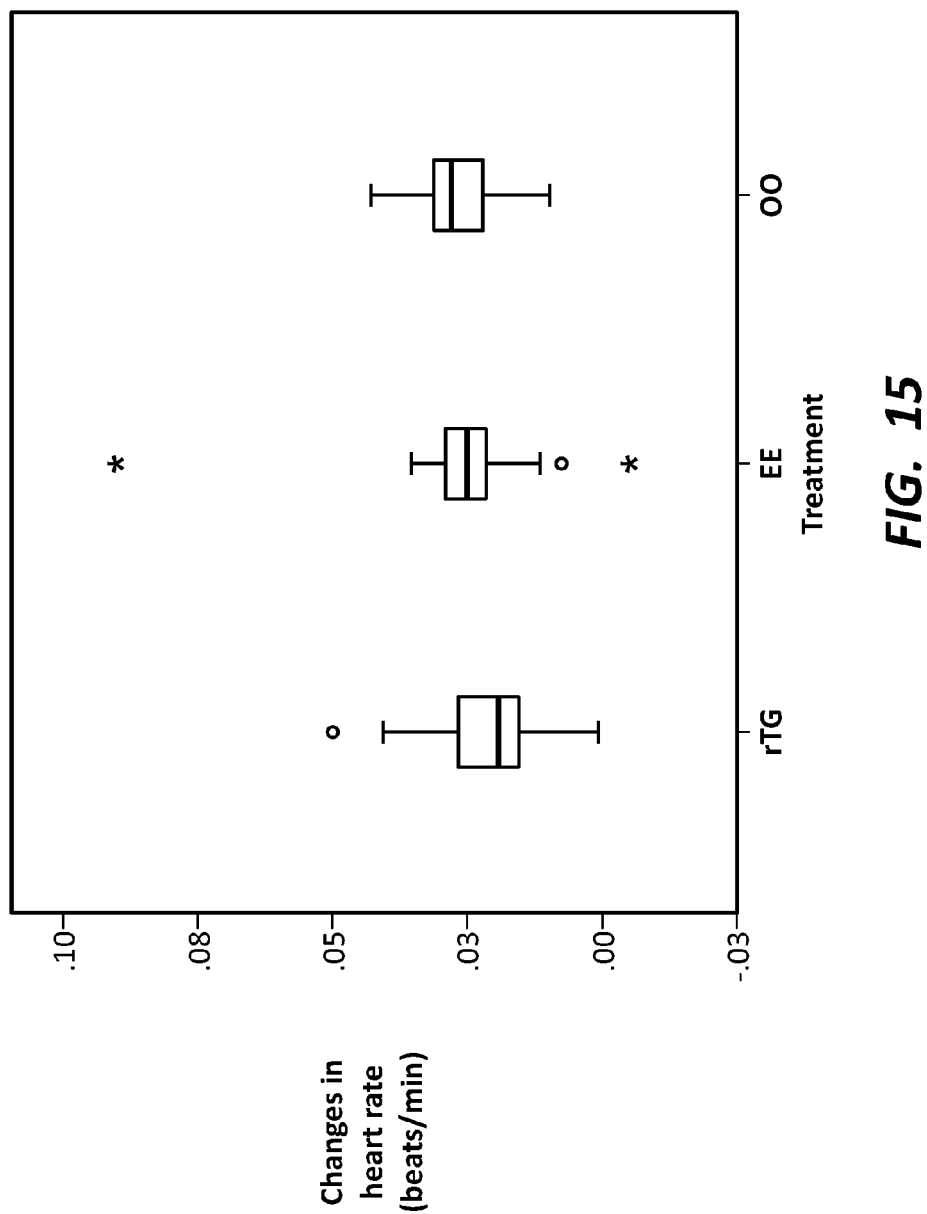
FIG. 15 is a box-and-whisker plot of the change in heart rate observed over the course of the study disclosed in Example 1.
Figure 16:
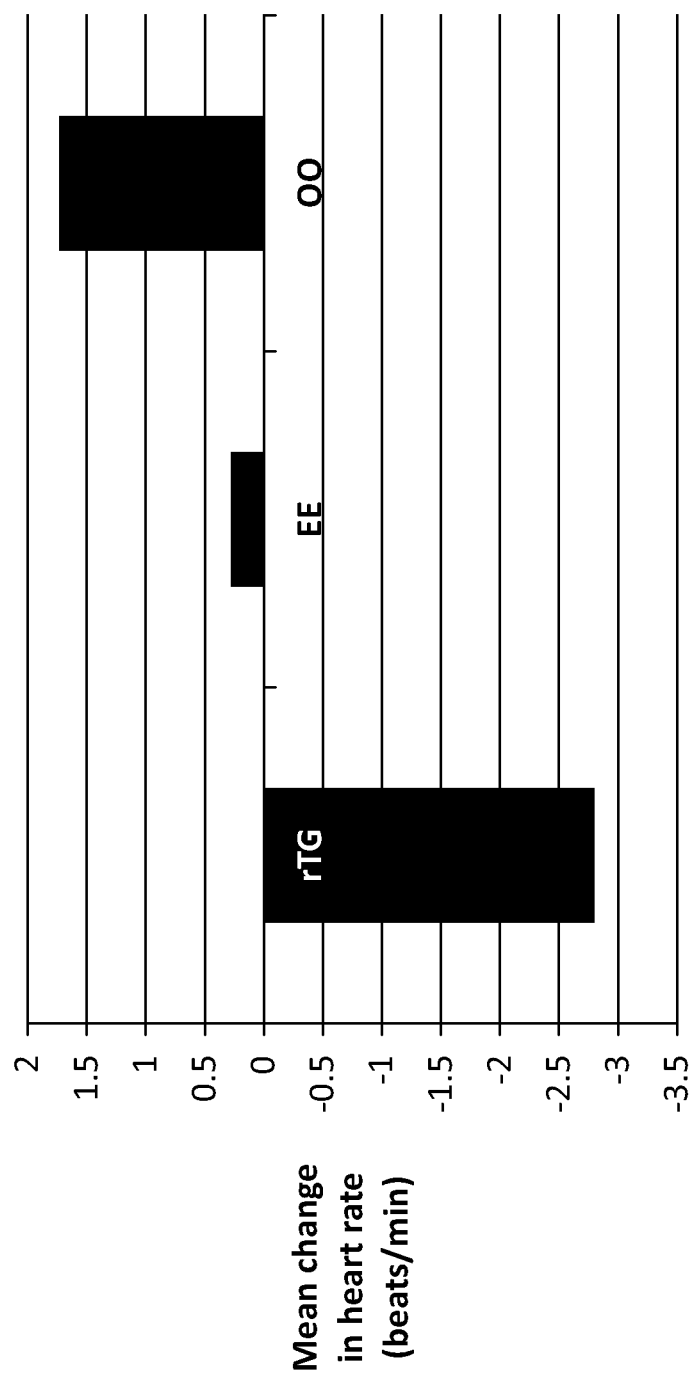
FIG. 16 is a bar graph depicting mean changes in heart rate for each arm of the study disclosed in Example 1.

FIGS. 15 and 16 provide graphical representations of heart rate data collected during the study. More particularly, FIG. 15 provides a box-and-whiskers plot of the changes in heart rate (beats/minute) between a baseline heart rate measured at the beginning of the study and a heart rate measured at the conclusion of the study. The box-and-whisker plot shows the median, upper and lower quartile, and maximum and minimum values (excluding outliers). Outliers are shown as circles or asterisks. As shown in FIG. 15, heart rate levels generally decreased in the rTG group, while heart rates of those in the EE and placebo (olive oil) groups did not decrease.

FIG. 16 is a bar graph depicting mean changes in heart rate (expressed in beats/minute) for each group of the study. The mean heart rate for those in the rTG arm decreased more than 2.5 beats per minute, while no decrease was observed in the EE and placebo groups. The decrease in heart rate in the rTG group was significant relative to both the placebo group (p-value=0.045) and the baseline values prior to treatment (p-value=0.038). Changes in heart rate in the EE and placebo groups relative to baseline values were not statistically significant.

Figure 17:
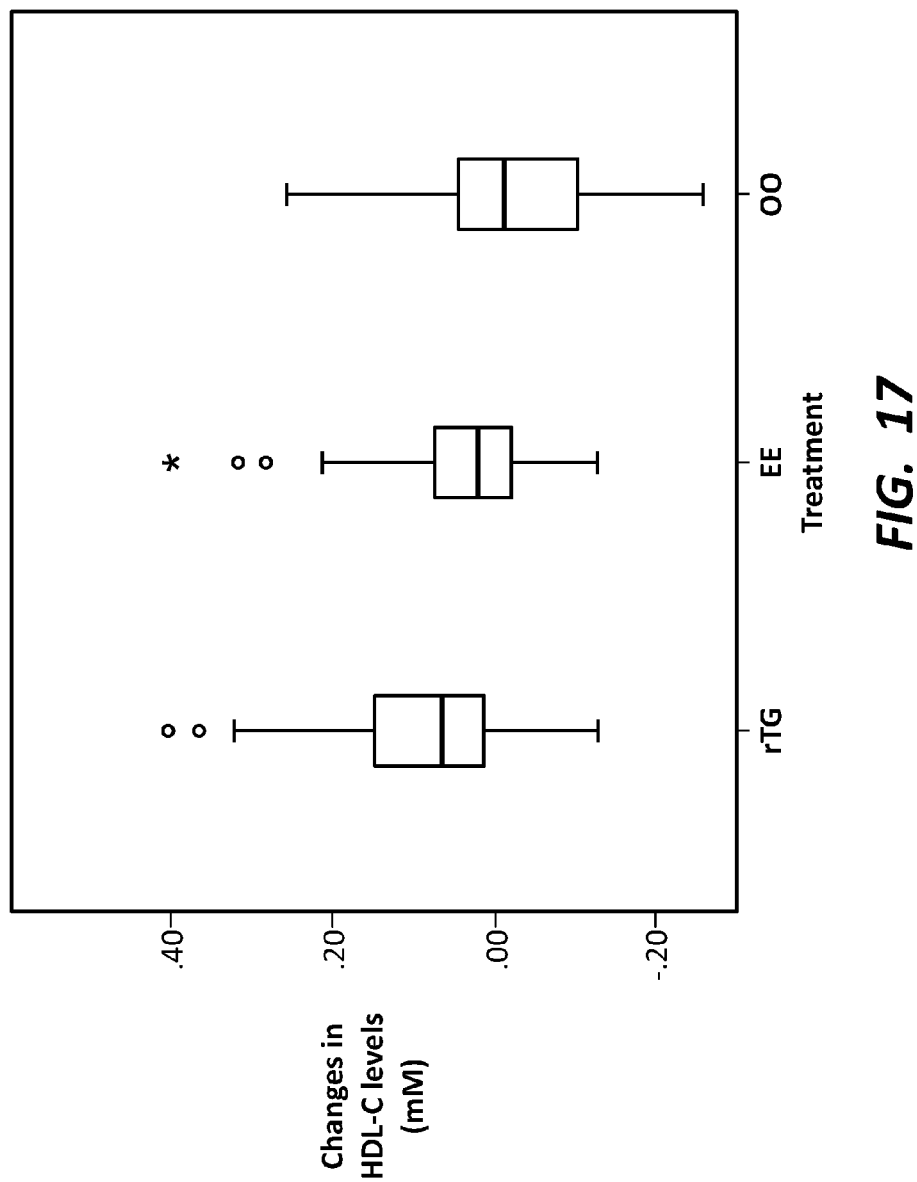
FIG. 17 is a box-and-whisker plot depicting changes in plasma high-density lipoprotein-cholesterol concentration over the course of the study disclosed in Example 1.
Figure 18:
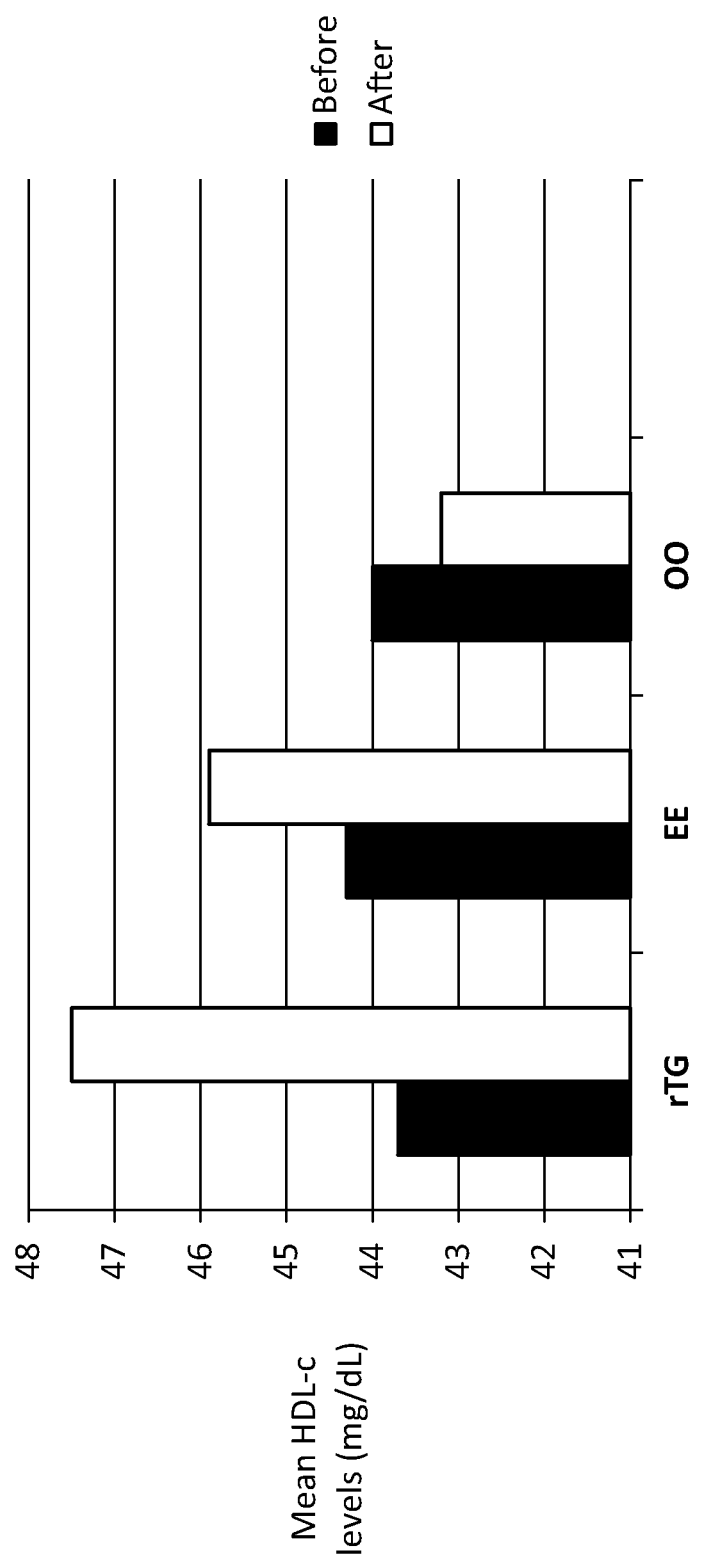
FIG. 18 is a bar graph depicting mean plasma high-density lipoprotein-cholesterol concentration at the beginning and at the conclusion of the study disclosed in Example 1.
Figure 19:
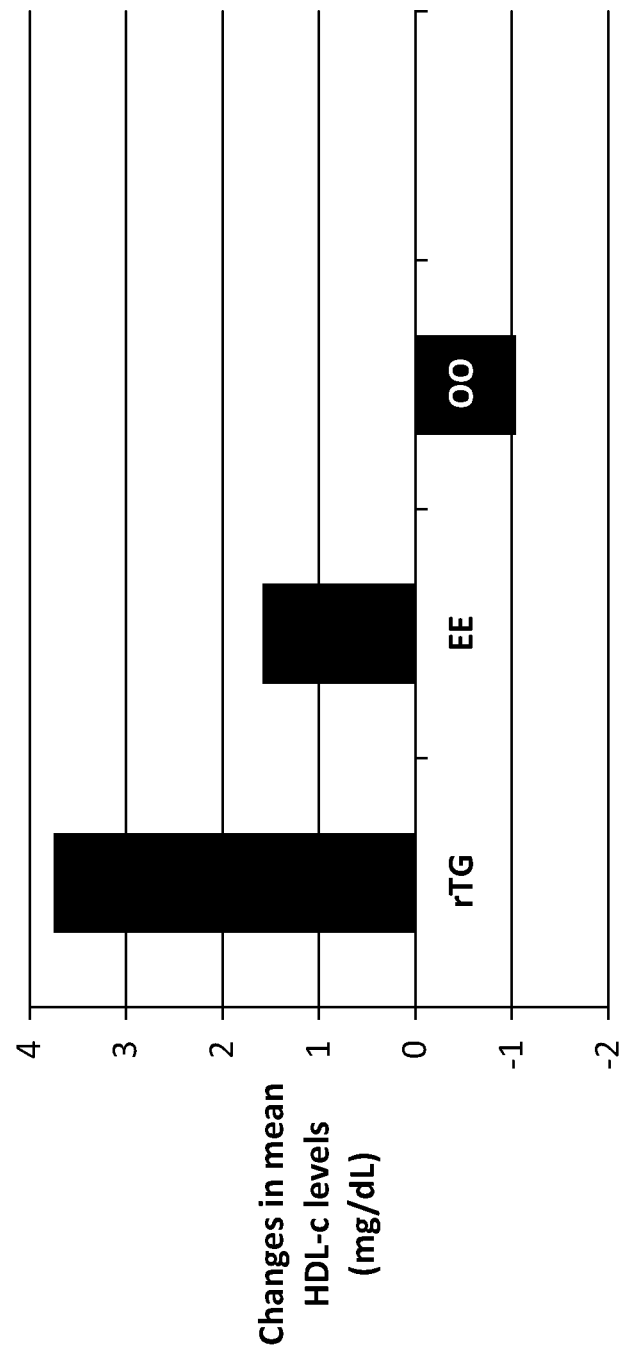
FIG. 19 is a bar graph depicting changes in mean plasma high-density lipoprotein-cholesterol concentration over the course of the study disclosed in Example 1.

FIGS. 17, 18, and 19 provide graphical representations of plasma high-density lipoprotein-cholesterol (HDL-c) concentration levels as measured during the study. More particularly, FIG. 17 provides a box-and-whisker plot that depicts, within each group, changes in plasma HDL-c levels (mM) between baseline levels measured at the beginning of the study and levels measured at the conclusion of the study. The box-and-whisker plot shows the median, upper and lower quartile, and maximum and minimum values (excluding outliers). Outliers are depicted with circles or asterisks.

As shown in FIG. 17, HDL-c concentrations in the blood plasma of those in the rTG and ethyl ester group generally increased, while the HDL-c concentrations of those in the placebo group generally did not increase.

FIG. 18 provides a bar graph of mean plasma HDL-c levels for each arm of the study. FIG. 19 is a bar graph depicting the changes in mean HDL-c concentrations within each group across the course of the study. These bar graphs show an increase in mean plasma HDL-c concentrations for those in the rTG and EE treatment arms, while the mean plasma HDL-c concentration for those in the placebo group decreased. The increase in HDL-c concentration within the rTG group was statistically significant relative to both the placebo group (p-value<0.001) and baseline values prior to treatment (p-value<0.001). The increase in HDL-c concentration within the EE group was also statistically significant relative to both the placebo group (p=0.025) and baseline values prior to treatment (p-value=0.026).

Figure 20:
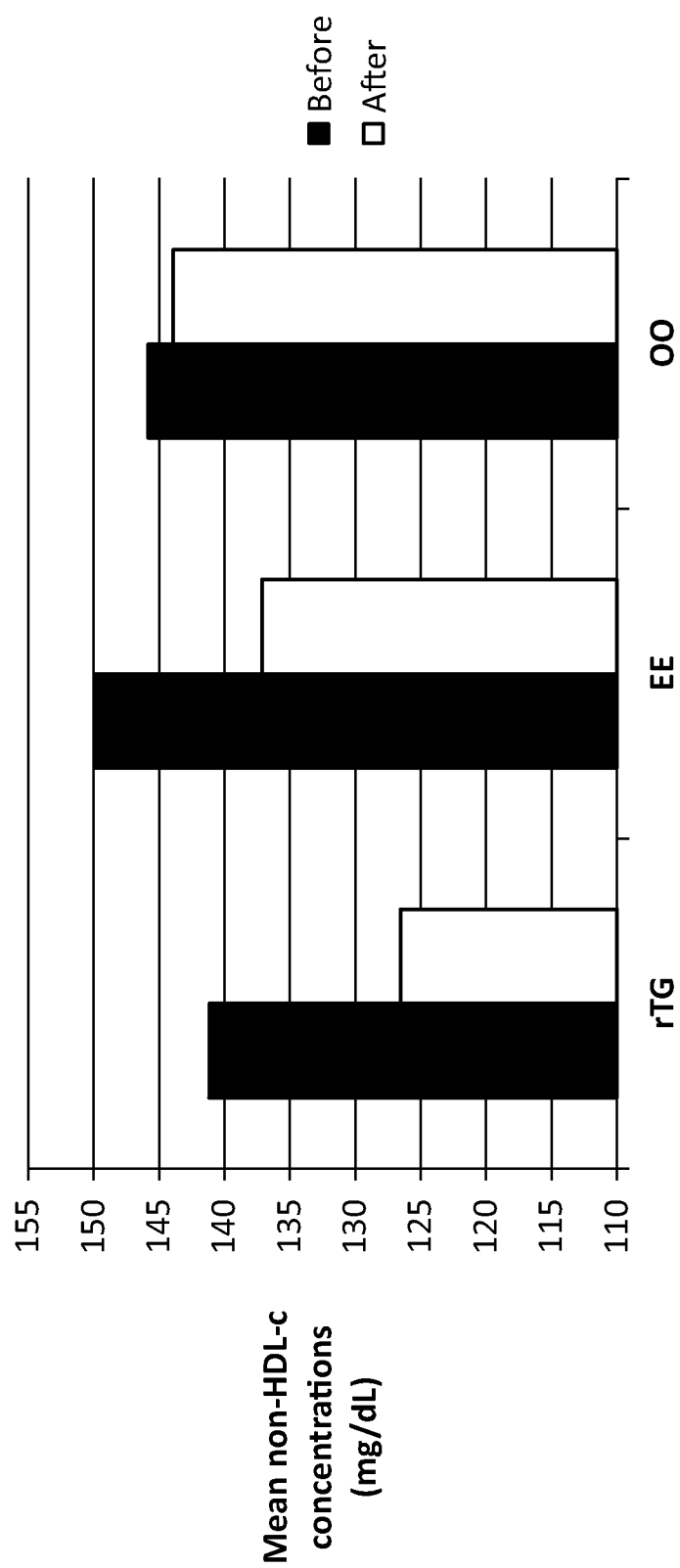
FIG. 20 is a bar graph of mean plasma non-high-density lipoprotein-cholesterol concentration for each arm of the study disclosed in Example 1.

FIG. 20 is a bar graph of mean plasma non-HDL-c concentrations (mg/dL) for each arm of the study. This bar graph shows a decrease in mean plasma non-HDL-c concentrations for those in the rTG and EE treatment arms relative to baseline (i.e., pre-treatment) values. The decrease in mean plasma non-HDL-c levels relative to baseline values is statistically significant for both the rTG and EE groups (p-values≤0.001). Additionally, the decrease in mean HDL-c concentrations for the rTG group was significant relative to the placebo group (p=0.027), while the decrease in mean HDL-c concentrations for the EE group was not statistically significant relative to the placebo group (p-value=0.064). Changes in non-HDL-c concentration within the placebo group were not statistically significant.

Figure 21:
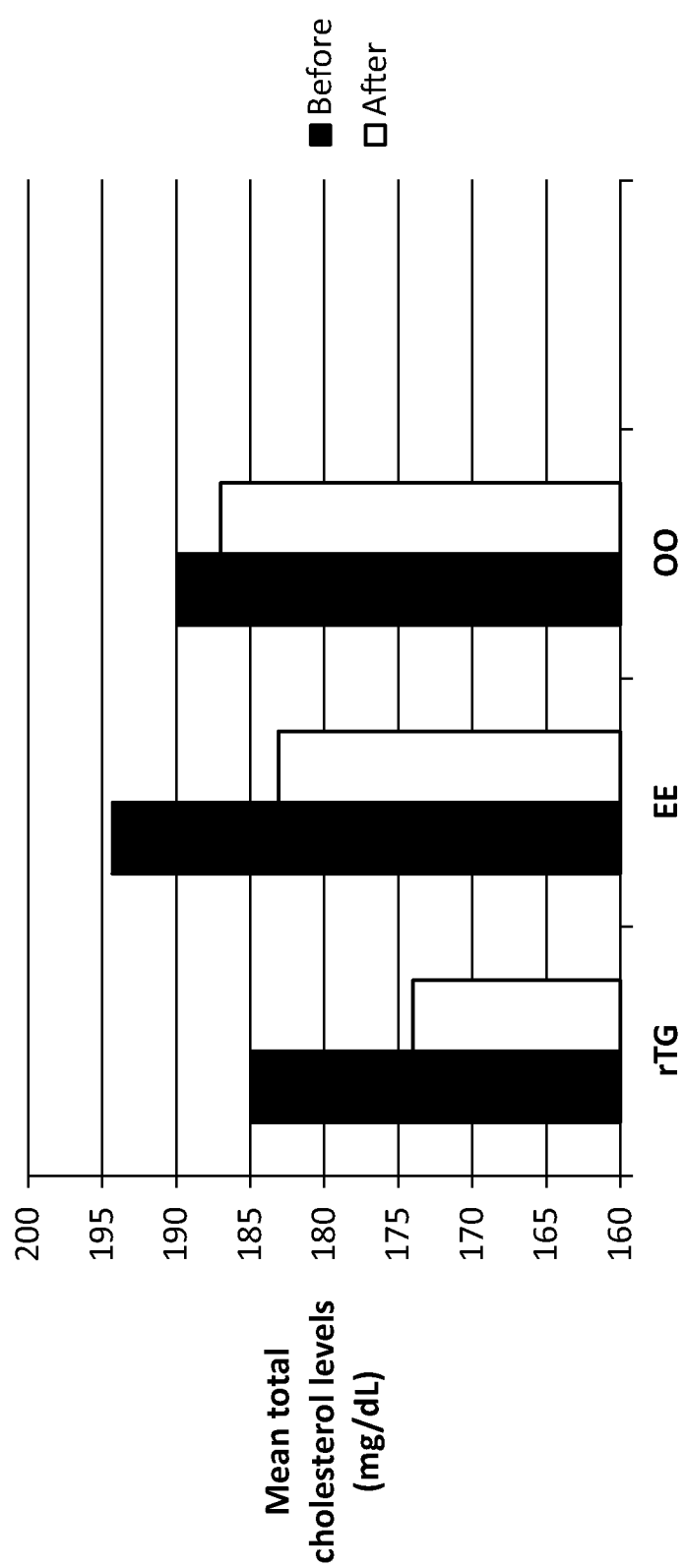
FIG. 21 is a bar graph depicting mean plasma total cholesterol levels for each arm of the study disclosed in Example 1.

FIG. 21 is a bar graph depicting mean plasma total cholesterol levels (mg/dL) for each arm of the study both at the beginning of the study (i.e., baseline values) and at the conclusion of the study. This bar graphs shows a decrease in mean plasma total cholesterol levels for those in the rTG and EE treatment arms relative to baseline (i.e., pre-treatment) values. The decrease in total cholesterol levels in these groups relative to baseline levels was statistically significant (p-values<0.05). However, neither the decrease in total cholesterol levels between the rTG and EE groups versus the placebo control (olive oil) nor the decrease in cholesterol levels within the placebo group relative to baseline levels was statistically significant. Likewise, the difference in the change in total cholesterol levels within the rTG group relative to the EE group was not statistically significant.

Figure 22:
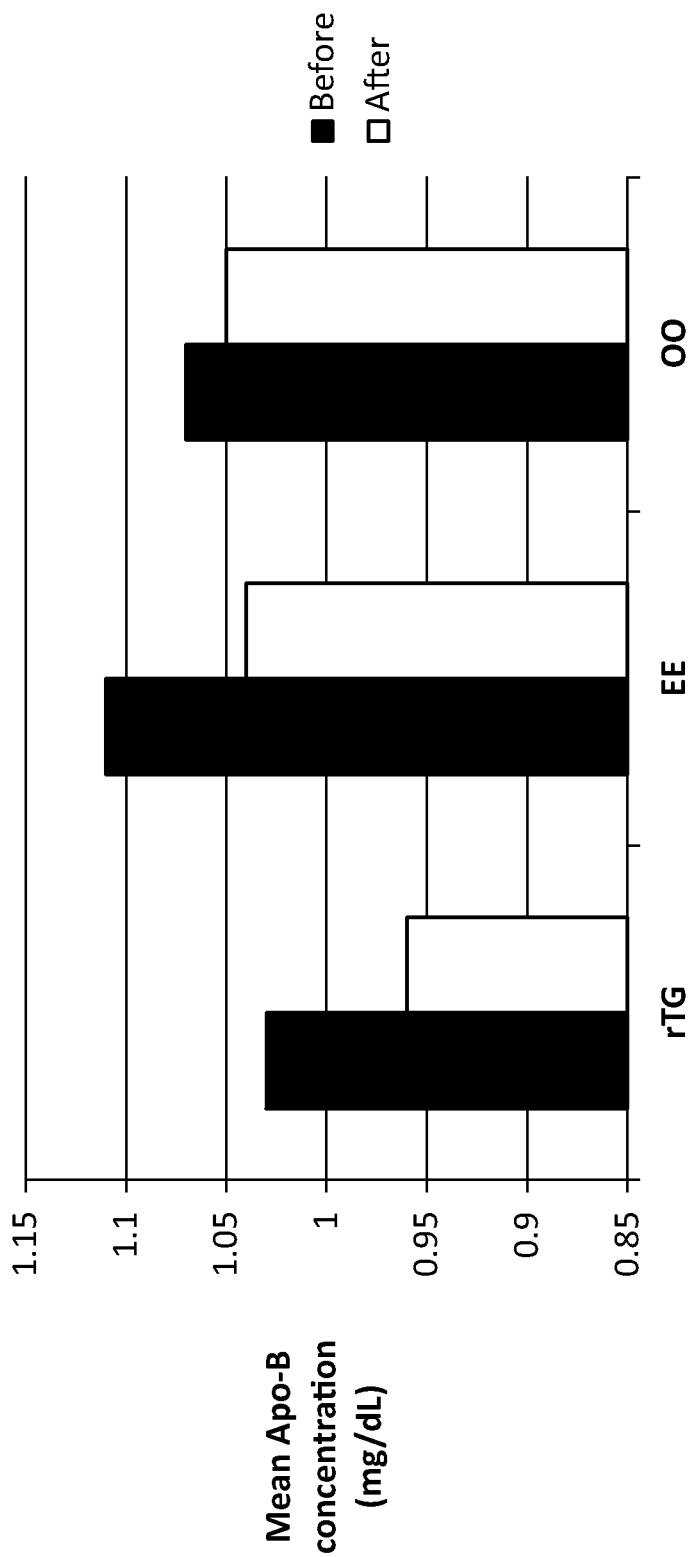
FIG. 22 is a bar graph depicting mean plasma apolipoprotein B concentrations for each arm of the study disclosed in Example 1.
Figure 23:
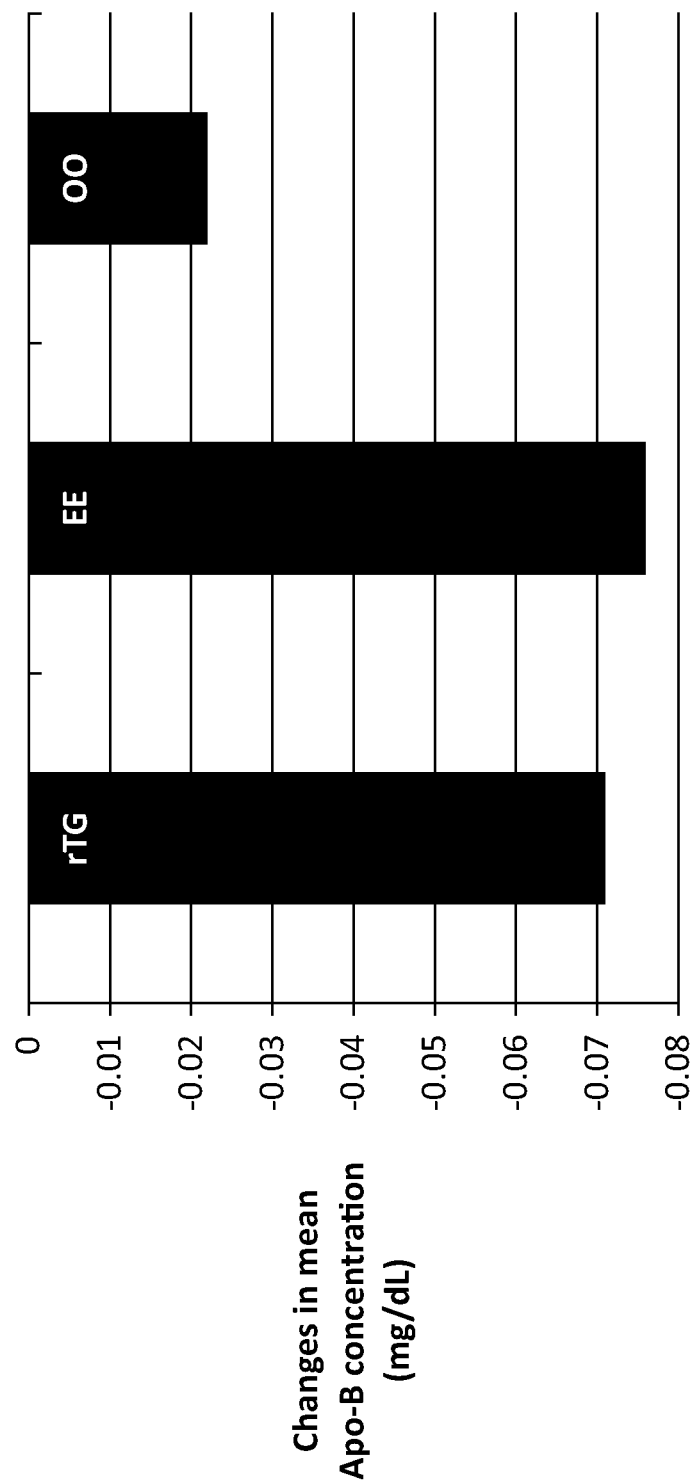
FIG. 23 is a bar graph depicting mean changes in plasma apolipoprotein B concentrations over the course of the study disclosed in Example 1.

FIGS. 22 and 23 provide graphical depictions of data related to blood plasma apolipoprotein B (Apo-B) concentration levels (mg/dL) in each arm of the study. More particularly, FIG. 22 is a bar graph depicting mean plasma Apo-B concentrations for each arm of at the beginning of the study (i.e., baseline levels) and at the conclusion of the study. FIG. 23 is a bar graph depicting the change in mean Apo-B concentrations in each arm across the study. The decrease in mean Apo-B concentrations shown in these figures was significant in both the rTG and EE groups relative to baseline (i.e., pre-treatment) levels (p-value<0.01). The change in mean Apo-B concentrations found in the rTG and EE groups relative to the olive oil placebo group was not statistically significant. The decrease in Apo-B concentrations found in the olive oil placebo group relative to baseline (i.e., pre-treatment) values was also not statistically significant.

Figure 24:
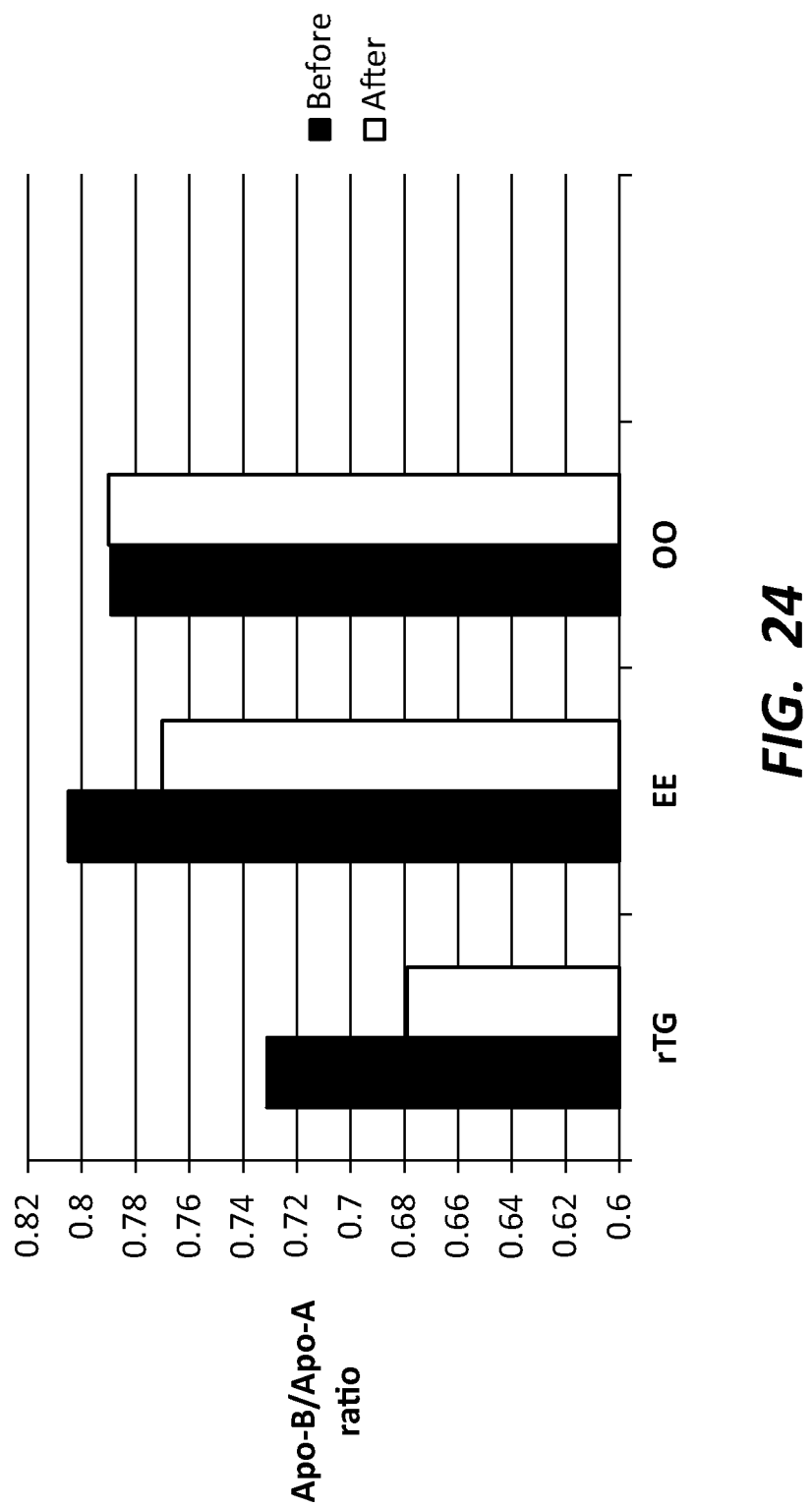
FIG. 24 is a bar graph depicting the ratio of plasma apolipoprotein B to apolipoprotein A for each arm of the study disclosed in Example 1.
Figure 25:
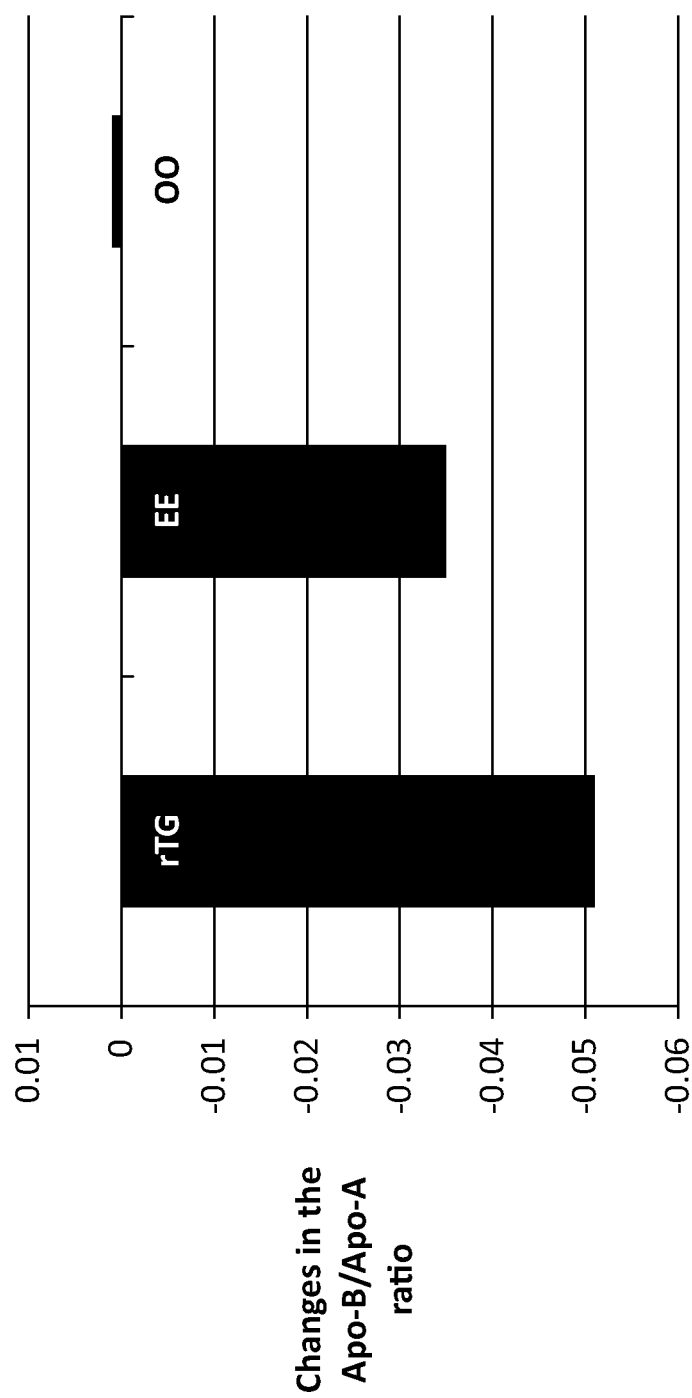
FIG. 25 is a bar graph depicting the changes in the apolipoprotein B/apolipoprotein A ratio across the course of the study disclosed in Example 1.

FIGS. 24 and 25 provide graphical depictions of data relating to the relative concentrations of Apo-B and apolipoprotein A (Apo-A) in the blood plasma of those in each arm of the study. More particularly, FIG. 24 is a bar graph depicting the mean ratio of Apo-B to Apo-A in each group, both at the beginning and at the conclusion of the study. FIG. 25 is a bar graph that depicts changes in mean plasma Apo-B/Apo-A concentration across the course of the study. These figures show a decrease in the mean plasma Apo-B/Apo-A ratio for both the rTG and EE groups. The decrease in the mean Apo-B/Apo-A ratio relative to baseline ratios in both the rTG and EE groups was statistically significant, with p-values of 0.003 and 0.008 respectively. The decrease in mean Apo-B/Apo-A ratios for the rTG groups was also statistically significant relative to the placebo group (p-value=0.027). The decrease in mean Apo-B/Apo-A ratios for the EE group was not statistically significant relative to the placebo group (p-value=0.182). Changes to the Apo-B/Apo-A ratio within the placebo group relative to baseline values were not statistically significant.

Figure 26:
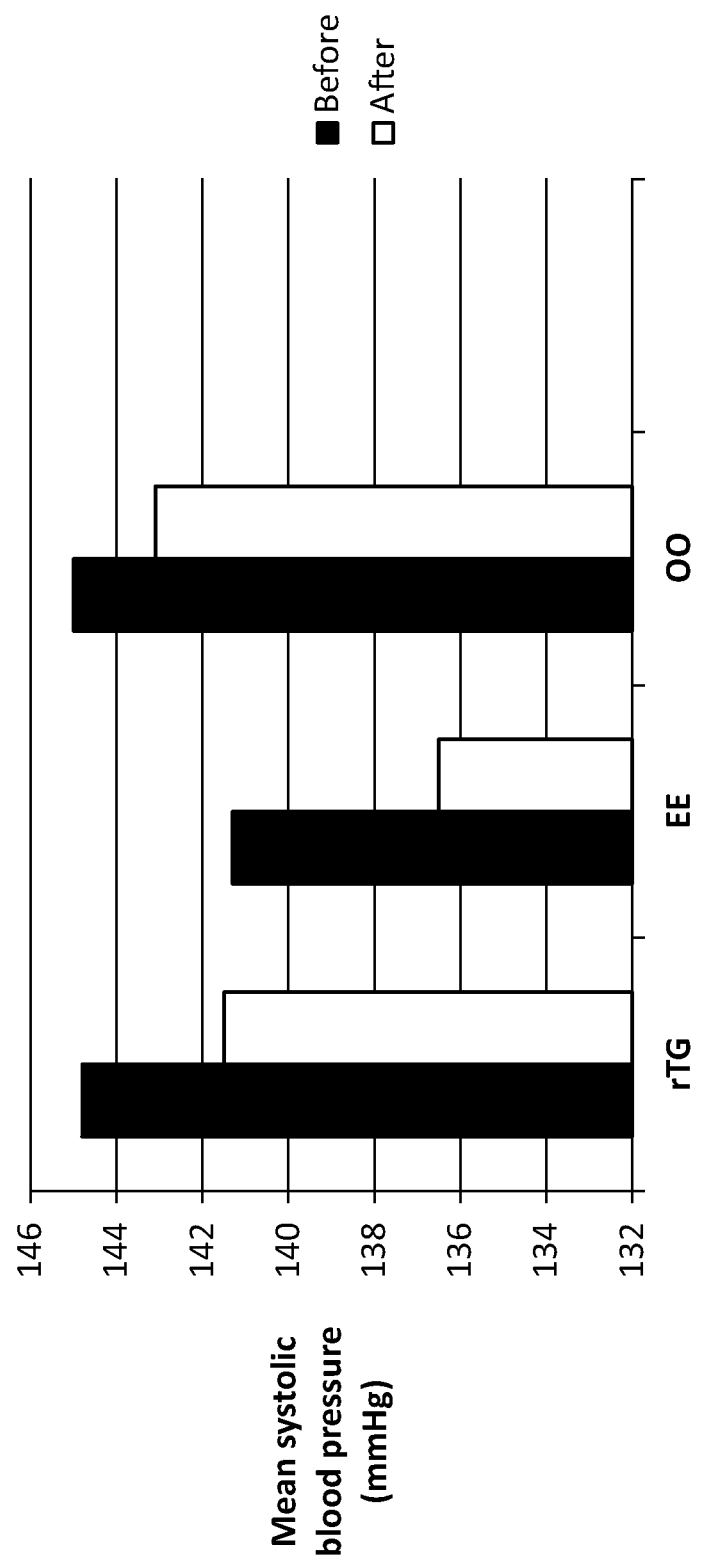
FIG. 26 is a bar graph depicting the systolic blood pressure in each arm of the study disclosed in Example 1.
Figure 27:
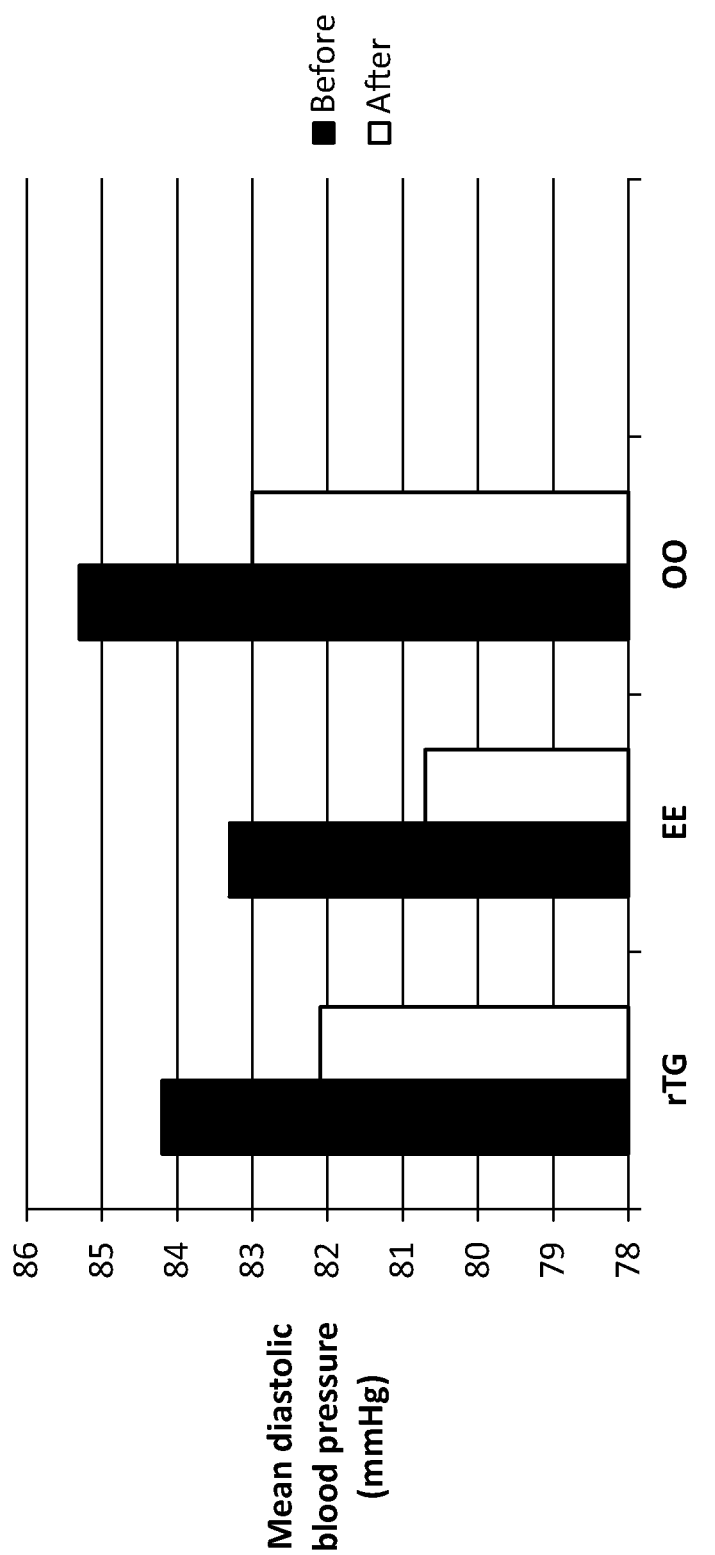
FIG. 27 is a bar graph depicting the diastolic blood pressure in each arm of the study disclosed in Example 1.

FIG. 26 is a bar graph depicting the mean systolic blood pressure in each group both at the beginning and at the conclusion of the study. FIG. 27 is a similar bar graph depicting the mean diastolic blood pressure in each group both at the beginning and at the conclusion of the study. The decrease in systolic and diastolic blood pressure within the rTG and EE groups relative to baseline levels was statistically significant (p-values<0.05). The changes in systolic and diastolic blood pressure in the rTG and EE groups relative to the placebo group (olive oil) were not statistically significant.

Figure 28:
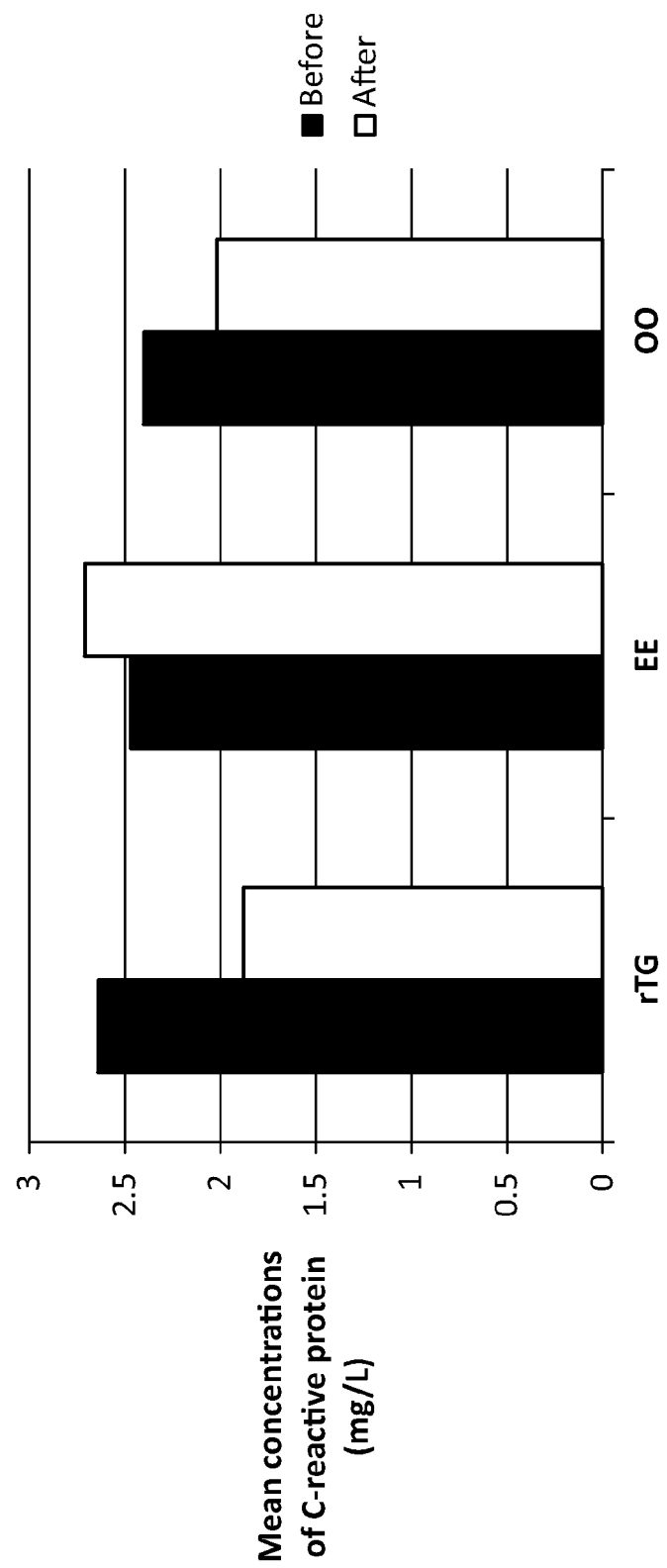
FIG. 28 is a bar graph depicting the mean plasma concentration of C-reactive protein in each arm of the study disclosed in Example 1.

FIG. 28 is a bar graph depicting the mean plasma concentrations of C-reactive protein (mg/L) in each arm of the study both at the beginning and at the conclusion of the study. The mean values of C-reactive protein were lowered in both the rTG group and the olive oil placebo group, but increased in the EE group. None of these changes in the rTG and EE groups was significant relative to baseline values or the placebo group.

Figure 29:
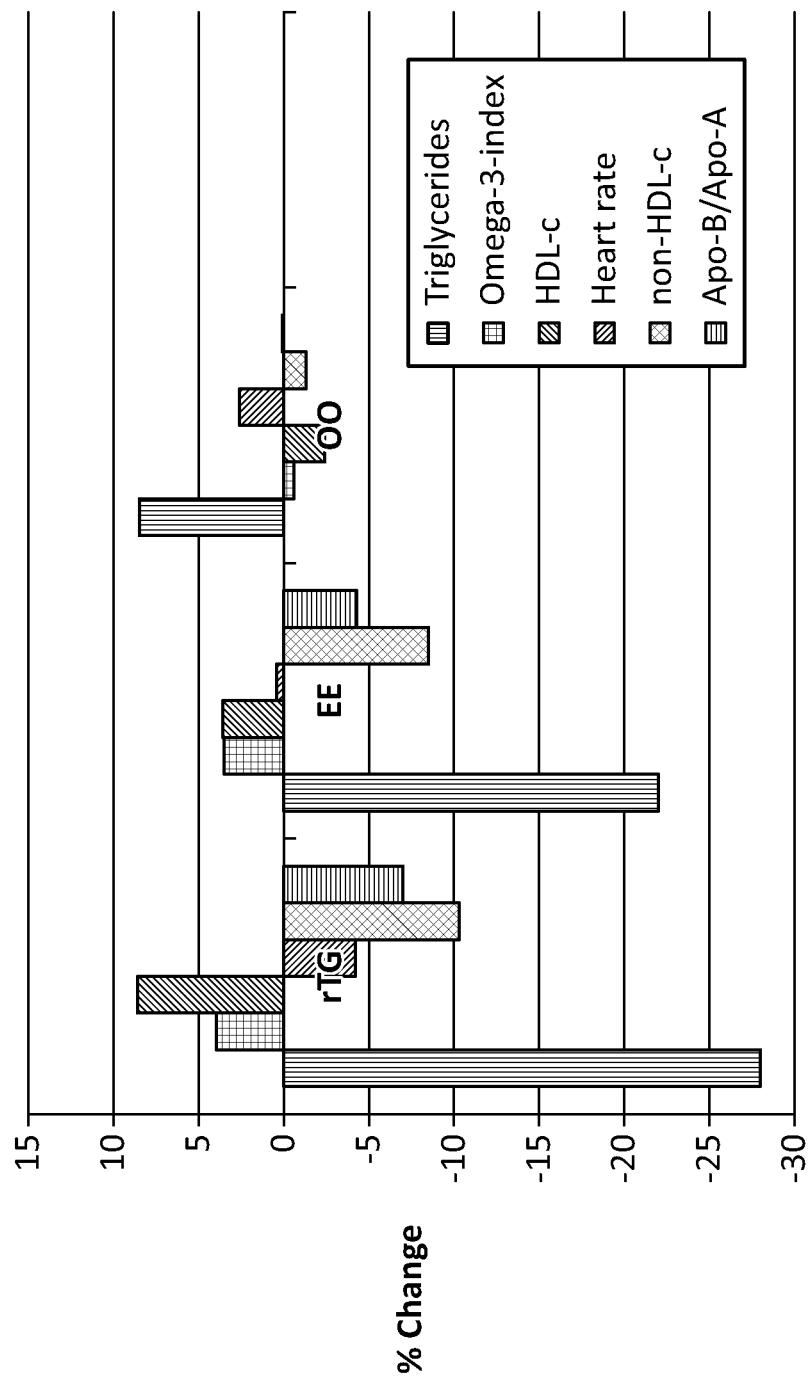
FIG. 29 is a bar graph depicting the percent change of various measurements and values determined over the course of the study disclosed in Example 1.

FIG. 29 is a bar graph depicting the percent change of the following measurements or values, relative to baseline (i.e., pre-treatment) levels: triglyceride concentration, HDL-c concentration, non-HDL-c concentration, the omega-3 index, heart rate, and the ratio of Apo-B to Apo-A.

Table 2 provides statistical data for between-group analyses (i.e., ANOVA-derived p-values) and within-group analyses (i.e., p-values derived from a paired t-test). In addition to the measurements, values, and indexes noted above, the table provides statistical data for changes in levels of alanine transaminase (ALAT), alkaline phosphatase, bilirubin, and HgbA1c. The table also provides statistical data for changes in the clotting tendency of the blood (as measured using the INR test) and the body mass index (BMI) of those in the study.

TABLE 2

| | Group difference, ANOVA, p-values two-tailed | | | Individual change, Paired t-test | | |
|---|---|---|---|---|---|---|
| | rTG vs. EE | rTG vs. OO | EE vs. OO | rTG (post-pre) | EE | OO |
| Triglyceride | 0.785 | <0.001 | <0.001 | <0.001 | <0.001 | 0.138 |
| Total cholesterol | 0.996 | 0.213 | 0.180 | 0.010 | <0.001 | 0.323 |
| HDL cholesterol | 0.088 | <0.001 | 0.025 | <0.001 | 0.026 | 0.131 |

TABLE 2-continued

| | Group difference, ANOVA, p-values two-tailed | | | Individual change, Paired t-test (post-pre) | | |
|---|---|---|---|---|---|---|
| | rTG vs. EE | rTG vs. OO | EE vs. OO | rTG | EE | OO |
| Non-HDL cholesterol | 0.930 | 0.027 | 0.064 | 0.001 | <0.001 | 0.521 |
| Apo-B/A ratio | 0.676 | 0.027 | 0.182 | 0.003 | 0.008 | 0.917 |
| Apo-A | 0.478 | 0.478 | 1.000 | 0.682 | 0.131 | 0.277 |
| Apo-B | 0.992 | 0.337 | 0.274 | 0.010 | 0.002 | 0.395 |
| Heart rate | 0.233 | 0.045 | 0.717 | 0.038 | 0.868 | 0.070 |
| Diastolic BP | 0.947 | 0.996 | 0.972 | 0.006 | 0.010 | 0.043 |
| Systolic BP | 0.805 | 0.807 | 0.420 | 0.050 | 0.006 | 0.258 |
| ALAT | 0.379 | 0.070 | 0.638 | 0.009 | 0.600 | 0.492 |
| Alkaline phosphatase | 0.837 | 0.110 | 0.311 | 0.003 | 0.026 | 0.863 |
| Bilirubin | 0.964 | 0.969 | 0.872 | 0.919 | 0.585 | 0.818 |
| CRP | 0.410 | 0.469 | 0.994 | 0.243 | 0.651 | 0.739 |
| INR | 0.068 | 0.031 | 0.999 | 0.021 | 0.604 | 0.239 |
| HgbA1c | 0.993 | 0.563 | 0.631 | 0.041 | 0.227 | 0.842 |
| BMI | 0.827 | 0.534 | 0.878 | 0.303 | 0.686 | 0.738 |
| DHA | <0.001 | <0.001 | <0.001 | <0.001 | <0.001 | 0.316 |
| EPA | 0.043 | <0.001 | <0.001 | <0.001 | <0.001 | 0.690 |
| O3 index | 0.788 | <0.001 | <0.001 | <0.001 | <0.001 | 0.173 |

Figure 30:
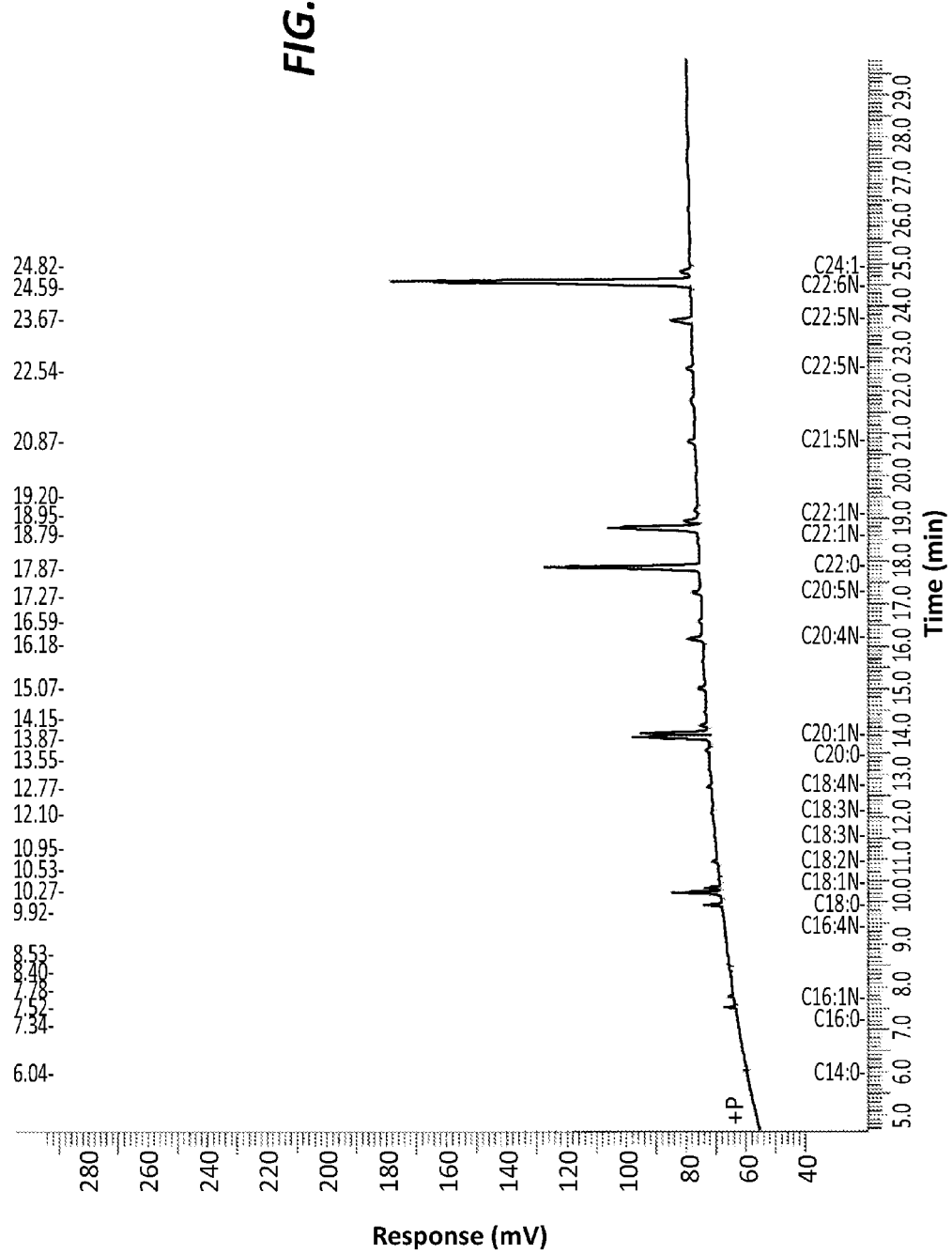
FIG. 30 is a chromatogram of oil used in the re-esterified triglyceride arm of the study disclosed in Example 1.

FIG. 30 and Table 3 provide information regarding the fatty acid composition of the oil prescribed to those in the rTG arm of the study. The oil was analyzed by gas-liquid chromatography to generate a fatty acid composition profile and to determine the relative concentrations of fatty acids in the oil. The resulting chromatogram is shown in FIG. 30, and data corresponding to the chromatogram are shown in Table 3. The percentages reported in Table 3 are relative to the total amount of detected fatty acids, and do not necessarily correspond with the total mass of the oil composition. As shown in this figure, the oil comprises a plurality of fatty acid compositions of varying length. The two most prevalent fatty acids in the composition are DHA (peak 29) and EPA (peak 22).

TABLE 3

| Peak # | Time | Component Name | Area [%] | Corrected Area [%] | Omega-3 Area [%] | Saturated FAC Area [%] | Mono-unsaturated FAC Area [%] | Poly-unsaturated FAC Area [%] |
|---|---|---|---|---|---|---|---|---|
| 1 | 6.035 | C14:0 | 0.13 | 0.1263 | 0.0000 | 0.1263 | 0.0000 | 0.0000 |
| 2 | 7.336 | | 0.07 | | | | | |
| 3 | 7.523 | C16:0 | 0.50 | 0.4839 | 0.0000 | 0.4839 | 0.0000 | 0.0000 |
| 4 | 7.781 | C16:1 n-7 | 0.31 | 0.3082 | 0.0000 | 0.0000 | 0.3082 | 0.0000 |
| 5 | 8.401 | | 0.06 | | | | | |
| 6 | 8.534 | | 0.08 | | | | | |
| 7 | 9.918 | C18:0 | 1.19 | 1.1554 | 0.0000 | 1.1554 | 0.0000 | 0.0000 |
| 8 | 10.213 | C18:1 n-9 | 3.26 | 3.1903 | 0.0000 | 0.0000 | 3.1903 | 0.0000 |
| 9 | 10.323 | C18:1 n-7 | 1.06 | 1.0641 | 0.0000 | 0.0000 | 1.0641 | 0.0000 |
| 10 | 10.530 | | 0.11 | | | | | |
| 11 | 10.949 | C18:2 n-6 | 0.40 | 0.3998 | 0.0000 | 0.0000 | 0.0000 | 0.3998 |
| 12 | 12.102 | C18:3 n-3 | 0.20 | 0.1960 | 0.1960 | 0.0000 | 0.0000 | 0.1960 |
| 13 | 12.707 | C18:4 n-3 | 0.39 | 0.3899 | 0.3899 | 0.0000 | 0.0000 | 0.3899 |
| 14 | 13.554 | C20:0 | 0.35 | 0.3468 | 0.0000 | 0.3468 | 0.0000 | 0.0000 |
| 15 | 13.867 | C20:1 n-11 | 6.93 | 6.9333 | 0.0000 | 0.0000 | 6.9333 | 0.0000 |
| 16 | 13.957 | C20:1 n-9 | 5.61 | 5.6066 | 0.0000 | 0.0000 | 5.6066 | 0.0000 |
| 17 | 14.150 | | 0.65 | | | | | |
| 18 | 15.014 | | 0.74 | | | | | |
| 19 | 16.179 | C20:4 n-6 | 1.63 | 1.6317 | 0.0000 | 0.0000 | 0.0000 | 1.6317 |
| 20 | 16.590 | | 0.34 | | | | | |
| 21 | 17.271 | C20:4 n-3 | 1.08 | 1.0842 | 1.0842 | 0.0000 | 0.0000 | 1.0842 |
| 22 | 17.871 | C20:5 n-3 | 16.58 | 16.5818 | 16.5818 | 0.0000 | 0.0000 | 16.5818 |
| 23 | 18.794 | C22:1 n-11 + 13 | 10.97 | 11.0829 | 0.0000 | 0.0000 | 11.0829 | 0.0000 |
| 24 | 18.947 | C22:1 n-9 | 1.50 | 1.4992 | 0.0000 | 0.0000 | 1.4992 | 0.0000 |
| 25 | 19.202 | | 0.42 | | | | | |
| 26 | 20.810 | C21:5 n-3 | 0.90 | 0.8992 | 0.8992 | 0.0000 | 0.0000 | 0.8992 |
| 27 | 22.545 | C22:5 n-6 | 0.85 | 0.8484 | 0.0000 | 0.0000 | 0.0000 | 0.8484 |
| 28 | 23.666 | C22:5 n-3 | 2.77 | 2.9399 | 2.9399 | 0.0000 | 0.0000 | 2.9399 |
| 29 | 24.587 | C22:6 n-3 | 39.63 | 40.0274 | 40.0274 | 0.0000 | 0.0000 | 40.0274 |
| 30 | 24.821 | C24:1 | 1.30 | 1.3788 | 0.0000 | 0.0000 | 1.3788 | 0.0000 |

Any methods disclosed herein may include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method described herein may be a separate method within the scope of this disclosure. Stated otherwise, some methods may include only a portion of the steps described in a more detailed method.

It will be apparent to those having skill in the art that changes may be made to the details of the above-described embodiments without departing from the underlying principles of the present disclosure.

The invention claimed is:

1. A composition comprising:
    a processed marine oil composition comprising fatty acid esters, wherein the fatty acid esters comprise esters of omega-3 polyunsaturated fatty acids (PUFAs), including esters of 4Z,7Z,10Z,13Z, 16Z,19Z-docosahexaenoic acid (DHA) and esters of 5Z,8Z,11Z,14Z,17Z-eicosapentaenoic acid (EPA);
    wherein a ratio of esters of DHA to esters of EPA is about 2.5:1 to about 4:1;
    wherein about 55 wt % to about 70 wt % of the fatty acid esters are in the form of triglycerides (TGs);
    wherein about 25 wt % to about 45 wt % of the fatty acids esters are in the form of diglycerides (DGs); and
    wherein the TGs and DGs are re-esterified triglycerides (rTGs) and re-esterified diglycerides (rDGs).

2. The composition of claim 1, wherein the ratio of esters of DHA to esters of EPA is about 5:2.

3. The composition of claim 1, wherein about 0 wt % to about 5 wt % of the fatty acid esters are in the form of monoglycerides (MGs).

4. The composition of claim 1, wherein about 5 wt % or less of the fatty acid esters are in the form of ethyl esters.

5. The composition of claim 1, wherein at least about 60 wt % of the fatty acid esters are esters of PUFAs.

6. The composition of claim 1, wherein at least about 50 wt % of the fatty acid esters are either esters of DHA or esters of EPA.

7. The composition of claim 1, wherein about 0 wt % to about 35 wt % of the fatty acid esters are esters of monounsaturated fatty acids.

8. The composition of claim 1, wherein about 0 wt % to about 5 wt % of the fatty acid esters are esters of saturated fatty acids.

9. The composition of claim 1, wherein at least about 15 wt % of the marine oil is derived from cephalopod oil.

10. A dosage form comprising:
    a processed marine oil composition comprising fatty acid esters, wherein the fatty acid esters comprise esters of omega-3 polyunsaturated fatty acids (PUFAs), including at least about 450 mg of esters of 4Z,7Z,10Z,13Z, 16Z,19Z-docosahexaenoic acid (DHA) and at least about 150 mg of esters of 5Z,8Z,11Z,14Z,17Z-eicosapentaenoic acid (EPA);
    wherein about 55 wt % to about 70 wt % of the fatty acid esters are in the form of triglycerides (TGs);
    wherein about 25 wt % to about 45 wt % of the fatty acid esters are in the form of diglycerides (DGs);
    wherein the TGs and DGs are re-esterified triglycerides (rTGs) and re-esterified diglycerides (rDGs).

11. The dosage form of claim 10, wherein a ratio of esters of DHA to esters of EPA is about 3:2 to about 4:1.

12. The dosage form of claim 10, wherein the amount of esters of DHA is about 450 mg to about 700 mg.

13. The dosage form of claim 10, wherein the amount of esters of EPA is about 150 mg to about 300 mg.

14. The dosage form of claim 10, wherein a mass of the dosage form is about 1200 mg to about 1600 mg.

\* \* \* \* \*